United States Patent
Kamphus et al.

(10) Patent No.: US 10,767,029 B2
(45) Date of Patent: Sep. 8, 2020

(54) AGGLOMERATED SUPERABSORBENT POLYMER PARTICLES COMPRISING CLAY PLATELETS WITH EDGE MODIFICATION AND/OR SURFACE MODIFICATION

(71) Applicant: The Procter & Gamble Company, Cincinnati, OH (US)

(72) Inventors: Juliane Kamphus, Schwalbach (DE); Arsen Simonyan, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 100 days.

(21) Appl. No.: 15/954,641

(22) Filed: Apr. 17, 2018

(65) Prior Publication Data

US 2018/0305517 A1    Oct. 25, 2018

(30) Foreign Application Priority Data

Apr. 19, 2017  (EP) .................................. 17167088
Mar. 20, 2018  (WO) ................ PCT/US2018/023276

(51) Int. Cl.
*B32B 5/16*     (2006.01)
*C08K 3/34*     (2006.01)
(Continued)

(52) U.S. Cl.
CPC .............. *C08K 3/346* (2013.01); *A61L 15/18* (2013.01); *A61L 15/24* (2013.01); *A61L 15/60* (2013.01);
(Continued)

(58) Field of Classification Search
CPC .. B01J 2220/68; B01J 20/267; B01J 20/3028; B01J 20/3282; B01J 20/28004
See application file for complete search history.

(56) References Cited

U.S. PATENT DOCUMENTS

| | | | |
|---|---|---|---|
| 4,340,706 | A | 7/1982 | Obayashi et al. |
| 4,666,983 | A | 5/1987 | Tsubakimoto et al. |

(Continued)

FOREIGN PATENT DOCUMENTS

| | | |
|---|---|---|
| EP | 083022 | 7/1983 |
| EP | 149880 A2 | 7/1985 |

(Continued)

OTHER PUBLICATIONS

Jalaii, et al., "Experimental study of the removal of copper ions using hydrogels of xanthan, 2-acrylamido-2-methyl-1-propane sulfonic acid, montmorillonite: Kinetic and equilibrium study", Carboyhydrate Polymers 142 (2016) 124-132.

(Continued)

*Primary Examiner* — Hoa (Holly) Le
(74) *Attorney, Agent, or Firm* — Brian M. Bolam

(57) ABSTRACT

Agglomerated superabsorbent polymer particles are provided and obtained by a method including the steps of: (a) providing precursor superabsorbent polymer particles having a first mass average particle size $^1$mAvPS, (b) mixing the precursor superabsorbent polymer particles with a solution, and (c) polymerizing the mixed solution if the solution includes polymerizable monomers and/or oligomers or crosslinking the mixed solution if the solution includes crosslinkable polymers. The solution includes (i) homogeneously dispersed therein, clay platelets with opposing basal platelet surfaces and platelet edges; (ii) one or more surface modification compound(s) and/or edge modification compound(s); and (iii) polymerizable monomers and/or oligomers, or (iv) crosslinkable polymers. The agglomerated superabsorbent polymer particles have a second mass average particle size $^2$mAvPS which is at least 25% greater than the first mass average particle size $^1$mAvPS.

13 Claims, 10 Drawing Sheets

260μm

(51) Int. Cl.
*C08K 7/00* (2006.01)
*C08J 3/20* (2006.01)
*A61L 15/24* (2006.01)
*A61L 15/18* (2006.01)
*A61L 15/60* (2006.01)
*C08J 3/12* (2006.01)

(52) U.S. Cl.
CPC .............. *C08J 3/12* (2013.01); *C08J 3/203* (2013.01); *C08K 7/00* (2013.01); *C08J 2333/02* (2013.01); *C08K 2201/005* (2013.01)

(56) References Cited

U.S. PATENT DOCUMENTS

| | | | |
|---|---|---|---|
| 5,331,059 | A | 7/1994 | Engelhardt |
| 5,409,771 | A | 4/1995 | Dahmen |
| 5,837,789 | A | 11/1998 | Stockhausen et al. |
| 5,849,816 | A | 12/1998 | Suskind et al. |
| 6,143,821 | A | 11/2000 | Houben |
| 6,472,478 | B1 | 10/2002 | Funk et al. |
| 6,503,979 | B1 | 1/2003 | Funk et al. |
| 6,911,499 | B1 | 6/2005 | Brehm et al. |
| 7,199,211 | B2 | 4/2007 | Popp et al. |
| 7,250,481 | B2 | 7/2007 | Jaworek et al. |
| 7,652,111 | B2 | 1/2010 | Hermeling et al. |
| 7,687,596 | B2 | 3/2010 | Hermeling et al. |
| 7,772,420 | B2 | 8/2010 | Hermeling et al. |
| 9,273,156 | B2 | 3/2016 | Takatori et al. |
| 2003/0105190 | A1 | 6/2003 | Diehl et al. |
| 2005/0165208 | A1 | 7/2005 | Popp et al. |
| 2005/0245393 | A1 | 11/2005 | Herfert et al. |
| 2008/0242817 | A1 | 10/2008 | Ducker et al. |
| 2009/0192035 | A1 | 7/2009 | Stueven |
| 2009/0258994 | A1 | 10/2009 | Stueven et al. |
| 2010/0068520 | A1 | 3/2010 | Stueven | |
| 2010/0234531 | A1* | 9/2010 | Frank ...................... B01J 20/26 525/192 |
| 2012/0157622 | A1* | 6/2012 | Lindner .................. A61L 15/60 524/790 |
| 2012/0271260 | A1 | 10/2012 | Azad et al. |
| 2015/0080821 | A1 | 3/2015 | Peri et al. |
| 2015/0328358 | A1 | 11/2015 | Kamphus et al. |
| 2016/0280825 | A1 | 9/2016 | Bauer et al. |

FOREIGN PATENT DOCUMENTS

| | | |
|---|---|---|
| EP | 530438 A1 | 3/1993 |
| EP | 547847 | 6/1993 |
| EP | 559476 A1 | 9/1993 |
| EP | 632068 A1 | 1/1995 |
| EP | 686650 A1 | 12/1995 |
| EP | 937736 A2 | 8/1999 |
| WO | WO9015830 | 12/1990 |
| WO | WO9321237 | 10/1993 |
| WO | WO01045758 A1 | 6/2001 |
| WO | WO02032962 A2 | 4/2002 |
| WO | WO2006069732 A1 | 7/2006 |
| WO | WO2006083584 | 8/2006 |
| WO | WO2012170778 | 12/2012 |
| WO | WO2015014826 A1 | 2/2015 |
| WO | WO2015175620 A1 | 11/2015 |

OTHER PUBLICATIONS

Bao, et al., "Swelling behaviors of organic/inorganic composites based on various cellulose derivatives and inorganic particles" Carbohydrate Polymers 88 (2012) 589-595.
International Search Report, PCT/US2018/023276, dated May 17, 2018, 18 pages.

\* cited by examiner

AGGLOMERATED SUPERABSORBENT POLYMER PARTICLES COMPRISING CLAY PLATELETS WITH EDGE MODIFICATION AND/OR SURFACE MODIFICATION

FIELD OF THE INVENTION

The present invention is directed to agglomerated superabsorbent polymer particles which have been formed by use of clay platelets with edge modification and/or surface modification, and to an absorbent article comprising the agglomerated superabsorbent polymer particles obtained via the method herein.

BACKGROUND OF THE INVENTION

The use of superabsorbent polymer particles, especially in absorbent articles, is well known in the art. The superabsorbent polymer particles are typically made by grinding or otherwise shredding relatively large blocks of superabsorbent polymer. However, the size of the particles obtained by such grinding or shredding cannot be fully controlled. The obtained superabsorbent polymer particles hence typically have a certain particle size distribution and thus, there are particles of relatively large size (e.g. 1000 µm or even larger) while others are considerably smaller, such as less than 100 µm or even significantly smaller, with the majority of the particle sizes ranging in between. Small particles are often referred to as "fines".

It is known that in order to have absorbent articles comprising superabsorbent polymer particles which exhibit good absorbing and containing functions, specific technical requirements need to be fulfilled by the superabsorbent polymer particles.

The superabsorbent polymer particles need first to be able to absorb the liquid exudates fast. The absorption speed of superabsorbent polymer particles has generally been characterized in the prior art by measuring the Free Swell Rate (FSR) of the particles.

In addition to having a high absorption speed, the superabsorbent polymer particles present in the absorbent core comprised by absorbent articles also need to be highly permeable to liquid. The permeability of the superabsorbent polymer particles has typically been characterized in the prior art by measuring the UPM (Urine permeability measurement) of the particles.

A poor permeability of the superabsorbent polymer particles may induce leakage of the absorbent article due to gel blocking. Gel blocking can occur in the absorbent core when swelling superabsorbent polymer particles block the void spaces between the particles. In such a case, the liquid exudates cannot or only slowly reach underneath layers of superabsorbent polymer particles disposed in the absorbent core. The liquid exudates remain on the surface of the absorbent core and may therefore leak from the absorbent article.

To address the problem of gel blocking, superabsorbent polymer particles are typically subjected to surface crosslinking, thus increasing the particle's stiffness and resistance to deformation upon swelling.

While surface cross-linking helps to increase the permeability of the superabsorbent polymer particles, the increase in permeability typically comes at the price of reduced capacity: Given the particles have a stiffer surface, they cannot swell as unhindered as non surface-cross-linked particles. This trade off is more pronounced for smaller superabsorbent polymer particles.

One way of reducing the number of fine particles without having to discard them is to form agglomerates of superabsorbent polymer particles.

The patent application US2010/0234531 of Evonik Stockhausen GmbH discloses a process for producing agglomerated superabsorbent polymer particles.

The patent application WO2015/175620 discloses agglomerated superabsorbent polymer particles which have been agglomerated by using a multivalent salt having a valence of three or higher.

Though several approaches to form agglomerated superabsorbent polymer particles have been described, there is still a need for an improved method of making agglomerated superabsorbent polymer particles as well as a need for improved agglomerated superabsorbent polymer particles.

SUMMARY OF THE INVENTION

Agglomerated superabsorbent polymer particles are disclosed, which are obtained by a method comprising the steps of a) providing precursor superabsorbent polymer particles having a first mass average particle size $^1$mAvPS, and b) mixing the precursor superabsorbent polymer particles with a solution comprising
  i) homogeneously dispersed therein, clay platelets with opposing basal platelet surfaces and platelet edges;
  ii) one or more surface modification compound(s) and/or edge modification compound(s); and,
  iii) polymerizable monomers and/or oligomers, or
  iv) crosslinkable polymers, c) polymerizing the mixed solution if the solution comprises polymerizable monomers and/or oligomers or crosslinking the mixed solution if the solution comprises crosslinkable polymers.

The agglomerated superabsorbent polymer particles have a second mass average particle size $^2$mAvPS which is at least 25% greater than the first mass average particle size $^1$mAvPS.

The first mass average particle size "$^1$mAvPS" is the mass average particle size of the precursor superabsorbent polymer particles according to the sieving test method described herein.

The second mass average particle size "$^2$mAvPS" is the mass average particle size of the agglomerated superabsorbent polymer particle according to the sieving test method described herein.

The invention also relates to an absorbent article comprising the agglomerated superabsorbent polymer particles obtained via the method described herein.

The agglomerated superabsorbent polymer particles having clay platelets with modified surfaces and/or edges show good performance properties. Especially, the agglomerated superabsorbent polymer particles may have a high permeability, a good absorption capacity and a high absorption speed. Indeed, the clay platelets with modified surfaces and/or edges linked to the precursor superabsorbent polymer particles sustain a certain force that increases the elongation to break of the agglomerated superabsorbent polymer particles. The agglomerated superabsorbent polymer particles having clay platelets with modified surfaces and/or edges can thus better resist deformation to avoid or reduce gel-blocking.

Moreover, due to the hydrophilic nature of the clay platelets with modified surfaces and/or edges, the clay platelets with modified surfaces and/or edges may avoid the aggregation of clays platelets that may be beneficial for the diffusion of liquid. Therefore, the resulting agglomerated superabsorbent polymer particles may have a good absorption speed.

DETAILED DESCRIPTION OF THE INVENTION

Figure 1:
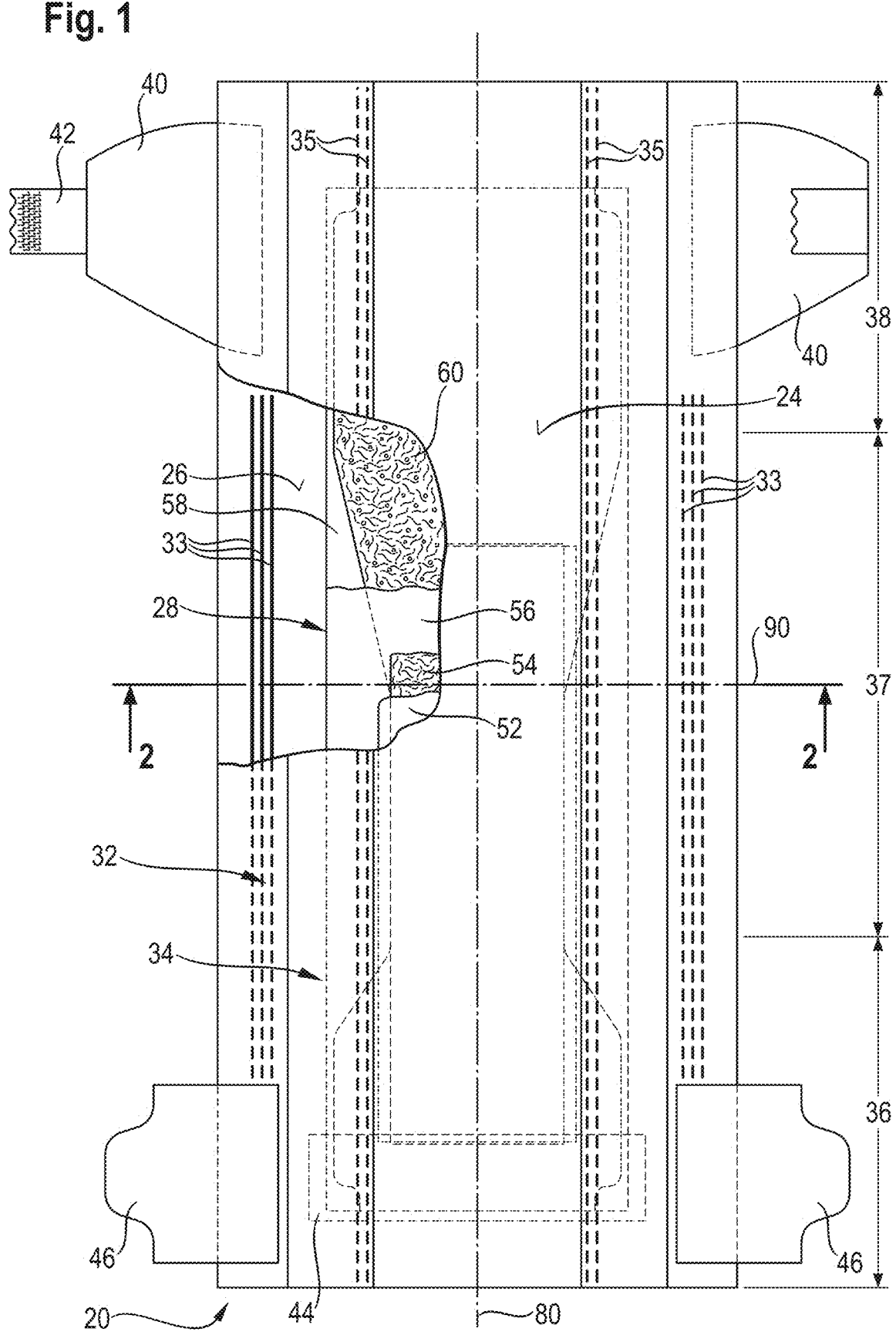
FIG. 1 is a top view of an exemplary absorbent article in the form of a diaper, which may comprise the agglomerated superabsorbent polymer particles of the present invention, with some layers partially removed.

The term "Absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. The term "exudates" includes, but is not limited to, urine, blood, vaginal discharges, sweat and fecal matter. Preferred absorbent articles of the present invention are disposable absorbent articles, more preferably disposable diapers and disposable pants.

"Disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasably) attaching the longitudinal edges of the first and second waist region to each other on both sides by a suitable fastening system.

"Absorbent core" is used herein to refer to a structure disposed between a topsheet and backsheet of an absorbent article for absorbing and containing liquid received by the absorbent article. If the absorbent article in addition to the absorbent core comprises a topsheet and/or a backsheet, and/or an acquisition system, the absorbent core does not include the topsheet, the backsheet and/or the acquisition system.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

Precursor Superabsorbent Polymer Particles

"Superabsorbent polymers" refer to absorbent material which are crosslinked polymeric materials that can absorb at least 10 times their weight of an aqueous 0.9% saline solution as measured using the Centrifuge Retention Capacity (CRC) test method (EDANA method NWSP 241.0.R2). These polymers are typically used in particulate forms ("water-absorbing polymer particles" or "superabsorbent polymer particles") so as to be flowable in the dry state. The term "particles" refers to granules, fibers, flakes, spheres, powders, platelets and other shapes and forms known to persons skilled in the art of superabsorbent polymer particles.

The precursor superabsorbent polymer particles useful for forming the agglomerated superabsorbent polymer particles of the present invention may be of numerous shapes.

The precursor superabsorbent polymer particles may be spherical-like superabsorbent polymer particles or ellipsoidal-like superabsorbent polymer particles or irregular-like superabsorbent polymer particles or fibers-like superabsorbent polymer particles, i.e. elongated, acicular superabsorbent polymer particles. In this specific embodiment, the precursor superabsorbent polymer particles fibers have a minor dimension (i.e. diameter of the fiber) of less than about 1 mm, usually less than about 500 µm, and preferably less than 250 µm down to 45 µm. The length of the fibers is preferably from about 3 mm to about 100 mm.

Preferably, the precursor superabsorbent polymer particles of the present invention and used for the formation of agglomerated superabsorbent polymer particles are spherical-like particles. According to the present invention and in contrast to fibers, "spherical-like particles" have a longest and a smallest dimension with a particulate ratio of longest to smallest particle dimension in the range of 1:5, where a value of 1 would equate a perfectly spherical particle and 5 would allow for some deviation from such a spherical particle.

The precursor superabsorbent polymer particles of the invention may have a particle size of from 45 to 850 µm, preferably from 45 to 500 µm, more preferably from 45 to 300 µm, even more preferably of less than 150 µm as measured according to EDANA method WSP 220.2-05.

The precursor superabsorbent polymer particles useful in the present invention include a variety of water-insoluble, but water-swellable polymers capable of absorbing large quantities of fluids. Such polymers materials are generally known in the art.

Preferred precursor superabsorbent polymer particles of the present invention are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

Typically, the precursor superabsorbent polymer particles comprise crosslinked polymers, preferably lightly cross-linked hydrophilic polymers. While these polymers may in general be non-ionic, cationic, zwitterionic or anionic, the preferred polymers are cationic or anionic.

Preferably, precursor superabsorbent polymer particles comprise acid polymers which contain a multiplicity of acid functional groups such as carboxylic acid groups or their salts, preferably sodium salts.

Preferably, the precursor superabsorbent polymer particles comprise crosslinked polymers of polyacrylic acids or their salts or polyacrylates or derivatives thereof.

Suitable precursor superabsorbent polymer particles may for example be obtained from inverse phase suspension polymerizations as described in U.S. Pat. Nos. 4,340,706 and 5,849,816 or from spray- or other gas-phase dispersion polymerizations as described in U.S. Patent Applications No. 2009/0192035, 2009/0258994 and 2010/0068520. In some embodiments, suitable precursor superabsorbent polymer particles may be obtained by current state of the art production processes as is more particularly described from page 12, line 23 to page 20, line 27 of WO 2006/083584.

The surface of the precursor superabsorbent polymer particles may be coated. The surface of the precursor superabsorbent polymer particles may be surface crosslinked.

The precursor superabsorbent polymer particles may comprise crosslinkers as described below for the solution. Preferably, the precursor superabsorbent polymer particles comprise the first type of crosslinkers.

The precursor superabsorbent polymer particles may comprise polymerization initiators system as described below for the solution.

The Solution

The solution comprises, homogeneously dispersed therein, clay platelets with opposing basal platelet surfaces and platelet edges, one or more surface modification compound(s) and/or edge modification compound(s) and polymerizable monomers and/or oligomers or crosslinkable polymers.

The solution may comprise water. The solution may comprise further solvents in addition to water, such as organic solvent.

The concentration of clay platelets in the solution may be less than 20% by weight of the dispersion, or less than 10% by weight of the dispersion, or less than 5% by weight of the dispersion or less than 1% by weight of the dispersion.

Clay and Clay Platelets

The present invention applies clay that can be dispersed as platelets in a solution such as an acidic aqueous liquid. The solution may be a neutralized aqueous liquid. The solution may be a neutralized acidic aqueous liquid. The clay particles are in the form of platelets, e.g. exfoliated or individual clay particles in the form of platelets, having a largest dimension and a smallest dimension. For example, the largest dimension to smallest dimension ratio may be at least 2:1 or at least 10:1 or at least 25:1, up to 200:1 or up to 500:1.

The clay platelets in the solution are preferably homogeneously dispersed, e.g. there is no significant aggregation or flocculation of the clay platelets.

Clay platelets have edge surfaces also referred to as "edges" and opposing basal platelet surfaces also referred to as "surfaces". The clay platelets are surface and/or edge-modified. This ensures that the clay platelets are dispersible in the solution. In particular, when the clay platelets are small, the clay platelets have a low aspect ratio. Having surface and/or edge modified clay platelets is very beneficial in order to avoid the risk of aggregation of clay platelets in the solution.

The clay platelets and the surface and/or edge-modified clay platelets in the solution may have a weight average largest particle size dimension (length) of less than 800 nm, preferably less than 500 nm, more preferably less than 300 nm, more preferably less than 200 nm, even more preferably less than 100 nm according to the use of a X-ray microscopy, for example, Xradia 810 Ultra 3D X-ray Microscope commercialized by Zeiss or by the use of the dynamic light scattering test method.

The dynamic light scattering test method is described in the article: Karpovich, A et al, "Determination of dimensions of exfoliating materials in aqueous suspensions", MethodsX, 2016, 3, 19-24. NMR relaxometry test method may also be used and is described in the same article above.

The clay platelets and the surface and/or edge-modified clay platelets in the solution may have a weight average largest particle size dimension (length) of at least 5 nm, preferably of at least 10 nm, more preferably of at least 20 nm according to the use of a X-ray microscopy, for example, Xradia 810 Ultra 3D X-ray Microscope commercialized by Zeiss or by the use of the dynamic light scattering test method.

When the clay platelets have a large size dimension, it may be beneficial to break the larger size clay platelets by using an ultrasonic treatment before assessing their weight average largest particle size dimension as described above The clay platelets and the surface and/or edge-modified clay platelets in the solution may have an aspect ratio of less than 300, preferably less than 200, more preferably less than 100. The aspect ratio of clay platelets and the surface and/or edge-modified clay platelets in the solution is generally more than 5, preferably more than 10.

The aspect ratio of clay platelet is the ratio of the largest dimension and the lowest dimension, orthogonal to it, of the clay platelet.

In the solution, the clay platelets may be present as individual platelets or may be present as small aggregates of, for example, 2 to 5 clay platelets which may be determined via removal of a micro-slice of the agglomerated superabsorbent polymer particles (via a ultramicrotome) which is then subjected to a cryo-TEM methods, known in the art or by the use of the dynamic light scattering test method.

The clay platelets may be purified before surface-modification and/or edge-modification, e.g. to remove metals etc., by methods known in the art. For example, the clay to be modified may be a di-octahedral or tri-octahedral clay.

Examples of suitable clay platelets are selected from the group consisting of kaolinite such as kaolin, illite such as glauconite, or smectite or montmorillonite including hectorite, laponite (i.e. synthetic clay), saponite, vermiculite or mixtures thereof.

Preferably, the clay platelets are montmorillonite, hectorite, laponite or mixtures thereof.

Preferably, the clay platelets are laponite.

The clay platelets have modified basal surface and/or modified edges. The surface and/or edge modification of the clay platelets may be done prior to adding the polymerizable monomers and/or oligomers or crosslinkable polymers or simultaneously with adding the polymerizable monomers and/or oligomers or crosslinkable polymers. To obtain the surface and/or edge-modified clay platelets, the clay platelets may be dispersed in a solution that comprises one or more surface modification compound(s) and/or edge modification compound(s), and/or the clay platelets may be dispersed in a solution, and the modification compound(s) may then be added to the dispersion, optionally also as solution or dispersion.

The ratio of clay platelets to the surface modification compound(s) and/or the edge modification compound(s) may be within the range of 1:1 to 100:1 (by weight, based on the weight of dry clay platelets and dry edge and/or surface modification compound(s)).

In the following, the surface modification compound(s) and/or the edge modification compound(s) are described as they are before addition to the clay platelets.

Edge Modification Compound(s)

When modifying the edges of the clay platelets, the exchangeable cations of the clay platelet edges may be replaced by the edge modification compound(s). Then, typically, the point of zero charge of the clay platelet edges is either shifted to a lower pH value, or the edge charge is made pH-independently neutral or pH-independently negative.

In addition, or alternatively, the edge modification compound may be a compound, which hinders and reduces aggregation of clay platelets.

The edge modification compound(s) may consist of one or more phosphorylation compounds. The phosphorylation compound(s) may be selected from the group consisting of: phosphate salts and/or derivatives thereof and/or acids forms thereof; condensed phosphate salts, and/or derivatives thereof and/or acids forms thereof, phosponic acid, derivatives thereof and salts thereof; and combinations thereof. For example, sodium pyrophosphate decahydrate may be suitably used. Organo-phosphor derivatives may also be useful.

The edge modification compound(s) may consist of one or more silanization compounds (also referred to as: silane compound).

The silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least one moieties are selected from the subgroup b) or subgroup c) and that not more than three moieties are selected from said subgroup a).

Preferably, the silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least from one to three moieties are selected from the subgroup a) and that at least one moieties are selected from the subgroup b) or subgroup c).

It may be beneficial that at least one of said moieties $R^{I}$, $R^{II}$, $R^{III}$, $R^{IV}$ is a moiety that is suitable to bond to the polymerizable monomer or polymerizable oligomer. For example, at least one of said moieties is an unsaturated moiety, such as vinyl. Preferably, the edge modification compound(s) is a silanization compound such as 7-Octenyldimethylmethoxysilane.

The edge modification compound(s) may consist of one or more fluorination compounds. Preferably, the edge modification compound(s) include fluoride salt. Preferably, the counterion M is a mono-valent counterion, such as sodium or ammonium.

The edge modification compound(s) may be a compound that sterically hinders from the aggregation of said platelet edges in order to reduce the risk of aggregation of the clay platelets in the solution, in addition to modifying the charge of the edges of the clay.

The edge modification compound(s) may have at least one moiety of at least 10 angstrom (A) or of at least 15 angstrom, or of at least 20 angstrom. Preferably the edge modification compound(s) have at least a moiety with a carbon chain of at least 6 carbon atoms, or at least 9 carbon atoms or at least 12 carbon atoms.

Other compounds to modify the edges of the clay platelets include epoxides. For example polyether clay platelets can be formed.

Preferably, the edge modification compound(s) consist(s) of one or more phosphorylation compounds, silanization compounds or fluorination compounds or combination thereof.

The edge-modification compound, in particular those described above as phosphorization, silanization or fluorination compounds, may have a further moiety or moieties that can ionically or covalently bind to the monomer or oligomer, or to the polymer formed; for example, the edge modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the edge modification compound not only binds to the edge of the clay platelet, but the compound(s) can also ionically or covalently bind to the polymers.

The clay platelets may not only be edge-modified to ensure homogeneous dispersion but the edge modification may further serve to strongly bind the clay platelets to the polymerizable monomers and/or oligomers or crosslinkable polymers, e.g. covalently or ionically Surface Modification Compound(s)

The surface modification compound(s) may be a compound that has a cationic moiety (and/or: cationic at the pH of the liquid herein and reaction herein), that can bind to the negatively charged basal surface of the clay platelet. The surface modified clay may have surface(s) that are neutral (at the pH of the carrier liquid).

The surface modification compound(s) may comprise an alkylated nitrogen moiety, or alkoxylated nitrogen moiety, including for example linear, branched or cyclic amino-, ammonium-compounds. A majority of the moieties may be cationic at the pH of the reaction liquid/reaction.

The surface modification compound(s) may have one or more moieties selected from amines or imines, including derivatives thereof, such as diamines or diimines and/or ethylene or poly- or oligo-ethylene derivatives thereof, including hexamethylene diamine and derivatives thereof, ethylendiamine and derivatives thereof, oligo-alkyleneimine and derivatives thereof, such as linear or branched polyethyleneimine, olig-etheramines and derivatives thereof, linear or branched amides, or mixtures thereof.

The surface modification compound(s) may have an acryl amide moiety. The surface modification compound(s) may have a urethane moiety (bond by hydrogen bonding to the negative basal surface) or further modifications thereof. Preferably, the surface modification compound(s) may have a cationically modified urethane moiety.

Especially preferred are moieties selected from linear or branched polyethyleneimine, hexamethylene diamine or ethylendiamine, or derivatives of any of these, or mixtures thereof.

The surface modification compound(s) may also be a cationically modified oligo- or poly-saccharides, or derivative thereof.

In addition, the surface modification compound(s) may have one or more further moiety that is or are hydrophilic. This can aid dispersion of the surface-modified clay in the solution and/or can further enhance the hydrophilicity, and hence affinity for hydrophilic fluids (e.g. urine, blood, saline water), of the agglomerated superabsorbent polymer particles. This may for example be anionic moiety, or —OH. Preferably, the surface modification compound(s) has at least one moiety that is an alkoxylated moiety, carboxylated moiety, or sulfonated moiety, or sulfated moiety, to further improve hydrophilicity.

The surface modification compound(s) may be such that, when chemically bound (for example electrostatic bond) to the clay platelet surfaces, they introduce a sterically hindering moiety (s), which hinders and hence reduces aggregation of clay platelets. Hence, the surface modification compound(s) may have a moiety that is sterically hindering aggregation. Preferably, the surface modification compound(s) has one or more moieties that can provide sterical hindrance, having at least 6 carbon atoms, and/or a length of at least 10 angstrom, or at least 15 angstrom. Preferably, the surface modification compound(s) has an oligomer chain moiety.

For example, the surface modification compound(s) may have oligo-alkyleneoxide (AO) moiety, such as a oligo-ethyleneoxide (EO) moiety, with an average number of AO (e.g. EO)-repeating units of at least 2 or at least 5 or at least 10, and up to 100, or up to 60 or up to 40. Preferably, the surface modification compound(s) has at least a moiety that is an oligo-ethoxylate with a number of 2 to 40 repeating units.

The surface modification compound(s), in particular those with a cationic group as described above, may have a further moiety or moieties that can ionically or covalently bind to the monomer or oligomer, or to the polymer formed thereby; for example, the surface modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the surface modification compound not only binds to the surface of the clay platelet, but the compound(s) can also ionically or covalently bind to the polymers. Thus, the clay platelets are not only surface-modified to ensure homogeneous dispersion but the surface modification further serves to strongly bind to the polymers, e.g. covalently or ionically. The surface modification compound described herein above, e.g. with a cationic group, may for example comprise a polymerizable moiety, such as an alkylene, e.g. ethylene; and/or the unsaturated moiety may for example be an ester of acrylic acid, and/or an alkylated derivatives of acrylic acid, such as methacrylic acid.

It may be useful to apply during the surface and/or edge modification step and/or after the surface and/or edge modification step, an ultrasonic treatment step, and/or mixing step; preferred is the application of (e.g. high) shear mixing. For example, a Y-Tron mixer can be used. The exfoliation of the clay platelet may also be affected by use of high-shear mixers, (such as CB Loedige mixers, Schugi mixers, Littleford mixers, Drais mixers). The tip speed of any such mixers may for example be from at least $20\ \text{ms}^{-1}$, or at least $30\ \text{ms}^{-1}$ to for example 45 or 40 or 35 $\text{ms}^{-1}$.

The surface and/or edge modification of the clay platelets may be done in any liquid. It may for example be done in water. Alternatively, the surface and/or edge modification may be done in the absence of water, e.g. preferably in an anhydrous liquid, e.g. anhydrous liquid with a dielectric constant larger than 40 preferentially more than 50, for example propylene carbonate or ethylene carbonate. Preferred may be that the liquid phase comprises at least 80% by weight of water, preferably at least 90% by weight or even 100% by weight of water.

Preferably, the surface and/or edge modification compound(s) modify the clay platelet prior to mixing with the polymerizable monomers and/or oligomers or crosslinkable polymers. It may be preferred to modify the clay platelet's surfaces and/or edge, and then to wash the resulting modified clay platelet, and/or filtrate, and/or submit to dialysis the modified clay platelet, prior to mixing with the polymerizable monomers and/or oligomers or crosslinkable polymers.

Polymerizable Monomers and/or Oligomers or Crosslinkable Polymers

The solution may comprise polymerizable monomers and/or oligomers which contain a multiplicity of functional groups such as charges groups (anionic, cationic) for example carboxylic acid groups or their salts, preferably sodium salts.

Preferably, the polymerizable monomers and/or oligomers comprise polymerizable monomers and/or oligomers of acrylic acids or their salts or acrylates or derivatives thereof.

Polymerizable monomers and/or oligomers may include for example ethylenically unsaturated carboxylic acids or their salts, such as acrylic acid, methacrylic acid, maleic acid, fumaric acid, tricarboxy ethylene, itaconic acid, ethylenically unsaturated phosphonic acid or their salts, ethylenically unsaturated sulfonic acid or their salts, or derivatives thereof, such as acrylamide with 2-acrylamido-2-methylpropane sulfonic acid, methacrylamide, acrylic esters and methacrylic esters.

Preferably, the polymerizable monomers and/or oligomers are selected from the group consisting of ethylenically unsaturated carboxylic acids such as methacrylic acid or its salts, or acrylic acid or its salts, ethylenically unsaturated phosphonic acids or their salts, ethylenically unsaturated sulfonic acids or their salts, or mixtures thereof.

Acrylic acid or its salts and methacrylic acid or its salts are particularly preferred polymerizable monomers and/or oligomers. Acrylic acid or its salts is most preferable.

The preparation of useful polymerizable monomers and/or oligomers are described in DE-A 199 41 423, EP-A 686 650, WO 01/45758 and WO 03/14300.

The polymerizable monomers and/or oligomers may be used in the solution at a level of at least 1% by weight to 90% by weight, preferably from 10% by weight to 60% by weight.

In addition to polymerizable monomers and/or oligomers, the solution may also comprise one or more polymerizable ethylenically and/or allylically unsaturated monomers copolymerizable with the polymerizable monomers and/or oligomers, i.e. polymerizable ethylenically unsaturated acid-functional monomers. Examples of copolymerizable ethylenically unsaturated monomers may be acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Alternatively, the solution may comprise crosslinkable polymers. Preferably, the solution comprises crosslinkable polymers. The crosslinkable polymers may include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide. Preferably, the crosslinkable polymers are polyacrylic acids or their salts or polyacrylates or derivatives thereof.

The crosslinkable polymers may have a weight average molecular weight determined by gel permeability chromatography of more than 8,000 g/mol, preferably within the range of 10,000 g/mol to 1,000,000 g/mol, more preferably within the range of 50,000 to about 750,000 g/mol and even more preferably within the range of 90,000 to 700,000 g/mol.

In addition to polymerizable monomers and/or oligomers or crosslinkable polymers, the solution may also comprise neutralizing agents. Neutralizing agents may be used, such as alkali metal hydroxides, alkali metal oxides, alkali metal carbonates or alkali metal bicarbonates and also mixtures thereof. Neutralizing agents may be ammonia, or amines derivatives, such as ethanolamine, diethanolamine, triethanolamine or dimethylaminoethanolamine. Sodium and potassium can be used as alkali metal salts. Preferably, neutralizing agents are sodium hydroxide, sodium carbonate or sodium bicarbonate and also mixtures thereof. Typically, neutralization is achieved by admixing the neutralizing agent as an aqueous solution or as an aqueous dispersion or else as a molten or as a solid material. The acid groups of the polymerizable monomers and/or oligomers or of the crosslinkable polymers are typically 0-100 mol %, preferably 25-100 mol %, more preferably 65-90 mol % and most preferably 68-80 mol % neutralized.

The solution can further comprise a co-solvent. Co-solvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

The solution can further comprise additives such as polyethylene glycol, polypropylene glycol, mixed polyalkoxylates, polyalkoxylates based on polyols such as glycerine, trimethylolpropane or butanediol, surfactants with a HLB of more than 10 such as alkyl polyglucosides or ethoxylated sugar esters such as polysorbates. The additives may reduce the hardness or the brittleness of the agglomerated superabsorbent polymer particles obtained by the method described herein.

First Type of Crosslinkers

The solution may comprise a first type of crosslinkers. The first type of crosslinkers may include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, comprise further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Preferably, the first type of crosslinkers comprises acrylate or acrylamide groups.

When the solution comprises a first type of crosslinkers, the solution also comprises polymerizable monomers and/or oligomers.

Preferably, the solution comprises a first type of crosslinkers with polymerizable monomers and/or oligomers.

Preferably, the solution comprises acrylate or acrylamide groups with polymerizable monomers and/or oligomers Preferably, the first type of crosslinkers is diacrylated, dimethacrylated, triacrylated or trimethacrylated multiply ethoxylated and/or propoxylated glycerols. Di- and/or triacrylates of 3- to 10-tuply ethoxylated glycerol are particularly advantageous. More preferably, the first type of the crosslinkers is di- or triacrylates of 1- to 5-tuply ethoxylated and/or propoxylated glycerol.

When the solution comprises a first type of crosslinkers, the solution may also comprise a polymerization initiator system in order to initiate the polymerization.

This polymerization initiator system may be added in solid or liquid form, for example as a solution or dispersion in a liquid such as an aqueous liquid, e.g. water.

This polymerization initiator system may comprise more than one type of compound to initiate the polymerization, or it may comprise a single type of compound.

The polymerization initiator system may include an activator, such as an activator compound or for example heat or radiation, including light radiation. Alternatively, no activation may be needed.

The polymerization initiator system can be appropriately selected from conventional (e.g. radical) polymerization initiators (and optional catalysts). Materials which display good water dispersibility/solubility are preferred. The polymerization initiator system may include peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis(2,4-dimethylvaleronitrile) and 2,2'-azobis(4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane)dihydrochloride,2,2'-azobis[2-(2-imidazolin-2yl)propane] dihydrochloride and 2,2'-azobis[2-(5-methyl-2-imidazolin-2-yl)propane] dihydrochloride. Very particular preference is given to 2,2'-azobis[2-(2-imidazolin-2-yl)propane] dihydrochloride and 2,2'-azobis [2-(5-methyl-2-imidazolin-2yl)propane] dihydrochloride.

More particularly, the polymerization initiator system may be persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. A mixture of two or more polymerization initiators may be used, for example one of the class of azo-compounds and one of the class of peroxo or peroxide compounds. This is believed to ensure fast polymerization. As described in US2008/242817, the use of azo compound initiator or redox initiators is advantageous for directing the rate of polymerization.

The polymerization initiator system may be introduced at a level of at least 0.001% by weight of the polymerizable monomers, preferably at least 0.01%, more preferably at least 0.02%, up to 0.1%, preferably up to 0.05% by weight of the polymerizable monomers.

The polymerization rate can be controlled through the identity and amount of the polymerization initiator compound used and the temperature used.

A polymerization catalyst may also be present, such as for example TMEDA (N,N,N',N' tetramethylethylenediamine). The polymerization of the polymerizable monomers may be highly exothermic so the polymerization liquid may be cooled during polymerization.

Second Type of Crosslinkers

Alternatively or additionally to the use of a first type of crosslinkers, the solution may comprise a second type of crosslinkers. The second type of crosslinkers may include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. A second type of crosslinkers may include the compounds from DE-A 40 20 780 cyclic carbonates, from DE-A 198 07 502 2-oxazolidone and its derivatives, such as N-(2-hydroxyethyl)-2-oxazolidone, from DE-A 198 07 992 bis- and poly-2-oxazolidones, from DE-A 198 54 573 2-oxotetrahydro-1,3-oxazine and its derivatives, from DE-A 198 54 574 N-acyl-2-oxazolidones, from DE-A 102 04 937 cyclic ureas, from DE-A 103 34 584 bicyclic amide acetals, from EP-A 1 199 327 oxetanes and cyclic ureas and from WO 03/031482 morpholine-2,3-dione and its derivatives.

Preferred second type of crosslinkers are amide acetals, carbamic esters, polyhydric alcohols like diols or polyols, cyclic carbonates, bisoxazolines, epoxides or Glycidyl Ethers such as Ethylene Glycol Diglycidyl Ether.

Preferred second type of crosslinkers are Glycidyl Ethers such as Ethylene Glycol Diglycidyl Ether.

When the solution comprises a second type of crosslinkers, the solution also comprises crosslinkable polymers.

Preferably, the solution comprises a second type of crosslinkers with crosslinkable polymers.

Preferably, the solution comprises Glycidyl Ethers such as Ethylene Glycol Diglycidyl Ether with crosslinkable polymers.

The solution can comprise the second type of crosslinkers in a quantity within the range of 0.001 wt. % to 30 wt. %, preferably within the range of 0.01 wt. % to 15 wt. %, more preferably within the range of 0.02 wt. % to 7 wt. % based on the weight of the solution.

The solution comprising clay platelets with modified surfaces and/or edges and polymerizable monomers and/or oligomers or crosslinkable polymers may have a viscosity determined according to ASTM 1824/90 at about 20° C. within a range of 50 mPa·s to 50,000 mPa·s, preferably within a range of 100 mPa·s to 20,000 mPa·s, more preferably within a range of 100 mPa·s to 5,000 mPa·s.

The high viscosity of the solution comprising polymerizable monomers and/or oligomers or crosslinkable polymers allows the neighboring precursor superabsorbent polymer particles, when mixed with the solution as described above, to be fixed together at specific points of contact between the particles. Therefore, the precursor superabsorbent polymer particles are not entirely coated with the solution but only in contact with the solution at specific points due to the viscosity of the solution. At these specific points of contact, the high viscosity of the solution enables the neighboring precursor superabsorbent polymer particles to be fixed together in order to form the agglomerated superabsorbent polymer particles. Relative strong bonds are created between the neighboring precursor superabsorbent polymer particles within the agglomerated superabsorbent polymer particles.

The solution may comprise from 0.1 to 10 wt % of clay platelets with modified surfaces and/or edges, from 5 to 95 wt. % of water; from 5 to 95 wt. % of polymerizable monomers and/or oligomers, from 0.001 to 10 wt. % of a first type of crosslinkers, optionally a dispersing aid, and from 0.001 to 5 wt. % of polymerization initiator to start the polymerization.

Alternatively, the solution may comprise from 0.1 to 10 wt % of clay platelets with modified surfaces and/or edges, from 5 to 95 wt. % of water; from 5 to 95 wt. % of crosslinkable polymers, from 0.001 to 10 wt. % of a second type of crosslinkers and optionally a dispersing aid.

Agglomerated Superabsorbent Polymer Particles

The present invention relates to agglomerated superabsorbent polymer particles. It has been surprisingly found that the use of a solution comprising clay platelets with modified surfaces and/or edges provides relatively high yields of agglomerated superabsorbent polymer particles with fast initial absorption speed while also having good capacity.

The clay platelets with modified surfaces and/or edges linked to the precursor superabsorbent polymer particles sustain a certain force that may increase the elongation to break of the agglomerated superabsorbent polymer particles. When the precursor superabsorbent polymer particles swell in the presence of bodily liquids, the agglomerated superabsorbent polymer particles having clay platelets with modified surfaces and/or edges can thus better resist deformation to avoid or reduce gel-blocking.

Moreover, having clay platelets with modified surfaces and/or edges avoid the agglomeration of clay platelets in order to improve the elongation to break of the agglomerated superabsorbent polymer particles and to improve the speed of absorption of bodily liquids of the agglomerated superabsorbent polymer particles.

Indeed, agglomerated superabsorbent polymer particles of the present invention may allow for less compacted agglomerates while still providing stable agglomerates. Due to the viscosity of the solution comprising clay platelets with modified surfaces and/or edges, the precursor superabsorbent polymer particles may be fixed to each other at only specific point of contact in order to avoid the compaction of agglomerates. By way of comparison, the reduced contact area sufficient to form stable agglomerates is similar to the use of relatively strong glue to bond different surfaces to each other. Stronger glues can be provided on a smaller surface area versus weaker glue where higher surface area coverage is required to obtained comparable bond strength.

The reduced contact area and reduced compaction may result in more surface area of the agglomerated superabsorbent polymer particles to absorb liquid in use, e.g. when the agglomerated superabsorbent polymer particles are used in absorbent articles. This, in turn, leads to agglomerated superabsorbent polymer particles with relatively high speed of absorption, which may be especially desirable in initial fluid uptake of agglomerated superabsorbent polymer particles, as is reflected by low uptake times.

The agglomerated superabsorbent polymer particles of the present invention may have an average swelling rate to reach 20 g/g of more than 1.00 g/g/s, preferably more than 1.05 g/g/s, more preferably more than 1.10 g/g/s according to the Free Swell Rate (FSR) test method described below, when the agglomerated superabsorbent polymer particles have a size below 850 lam, preferably a size between 300 µm and 850 µm.

The agglomerated superabsorbent polymer particles of the present invention may have an average swelling rate to reach 20 g/g of more than 0.50 g/g/s, preferably more than 0.75 g/g/s, more preferably more than 0.90 g/g/s according to the Free Swell Rate (FSR) test method described below, when the agglomerated superabsorbent polymer particles have a size above 850 µm, preferably a size between 850 µm and 1250 µm.

Absorbent articles comprising agglomerated superabsorbent polymer particles with good swelling rate and low uptake times, have improved absorption properties and therefore exhibit reduced leakage in comparison with absorbent articles of the prior art, especially at the first gush (i.e. first liquid insult). Hence, such agglomerated superabsorbent polymer particles are particularly suitable for use in absorbent articles.

The agglomerated superabsorbent polymer particles of the present invention may have a permeability at equilibrium expressed as UPM (Urine Permeability Measurement) value of more than 5, preferably more than 15, preferably more than 30, preferably more than 40, more preferably more than 60, more preferably more than 70, or even more preferably more than 80 UPM units according to the UPM test method, where 1 UPM unit is $1 \times 10^{-7}$ (cm$^3$·s)/g.

The agglomerated superabsorbent polymer particles of the present invention may have a permeability at equilibrium expressed as UPM (Urine Permeability Measurement) value of from 40 UPM to 500 UPM, preferably from 50 UPM to 400 UPM, more preferably from 80 UPM to 400 UPM according to the UPM test method described below.

The UPM Test method measures the flow resistance of a pre-swollen layer of superabsorbent polymer particles, i.e. the flow resistance is measured at or close to equilibrium. Therefore, agglomerated superabsorbent polymer particles having high UPM values exhibit a high permeability. High permeability is especially desirable in absorbent articles, when a significant volume of the absorbent article is already wetted by the liquid exudates. These absorbent articles exhibit good absorption properties not only at the first gush but also at the subsequent gushes.

Moreover, the Centrifuge Retention Capacity (CRC) measures the liquid absorbed by the agglomerated superabsorbent polymer particles for free swelling in excess liquid.

The agglomerated superabsorbent polymer particles of the invention may have a Centrifuge Retention Capacity (CRC) value of more than 20 g/g, preferably more than 25 g/g, preferably more than 26 g/g, more preferably more than 27 g/g, or even more preferably more than 29 g/g as measured according to the CRC test method (EDANA method NWSP 241.0.R2).

The agglomerated superabsorbent polymer particles of the invention may have a Centrifuge Retention Capacity (CRC) value of from 18 g/g to 40 g/g, preferably from 22 g/g to 40 g/g, more preferably from 25 to 38 g/g as measured according to the CRC test method (EDANA method NWSP 241.0.R2).

The agglomerated superabsorbent polymer particles of the present invention can be made as follows:

a) Precursor Superabsorbent Polymer Particles are Provided Having a First Mass Average Particle Size $^1$mAvPS:

Further, for purposes of this invention, the mass average particle size of the precursor superabsorbent polymer particles (for the first mass average particle size $^1$mAvPS) or the agglomerated superabsorbent polymer particles (for the second mass average particle size $^2$mAvPS) is defined as the particle size which is the average particle size of the given precursor superabsorbent polymer particles (or agglomerated superabsorbent polymer particles) on a mass basis. A method for determining the mass average particle size is described hereinafter in the Test Methods section. The mass average particle size of the precursor superabsorbent polymer particles (or agglomerated superabsorbent polymer particles) may be from 45 µm to 850 µm, or from 100 µm to 650 µm, or from 200 µm to 600 µm as long as the second mass average particle size $^2$mAvPS is at least 25% higher than the first mass average particle size $^1$mAvPS.

The precursor superabsorbent polymer particles having the first mass average particle size $^1$mAvPS may be any precursor superabsorbent polymer particles. However, it may be desirable to use precursor superabsorbent polymer particles which have been classified. For example, the precursor superabsorbent polymer particles may have been classified such that they have a defined an upper particle size limit. The upper particle size limit may be 500 µm, or 400 µm, or 300 µm, or 150 µm.

Classification is well known in the art and is typically done by sieving the particles using a defined mesh size. The particles passing the sieve will have a particle size lower than the mesh size used while the particles not passing through the sieve will (mostly) have a particle size equal to or larger than the mesh size. As will be understood, if too many precursor superabsorbent polymer particles are sieved simultaneously, some of the precursor superabsorbent polymer particles not passing through the sieve may nevertheless have a particle size smaller than the mesh size. Hence, as is understood by the skilled person, it is important to carefully and diligently carry out the sieving, not using too many precursor superabsorbent polymer particles at a time.

Moreover, the shape of the precursor superabsorbent polymer particles or agglomerated superabsorbent polymer particles to be sieved also impacts the accurateness of sieving. For particles or agglomerates having very irregular shape, their current orientation may determine whether or not they pass through a given mesh size. Hence, sieving precursor superabsorbent polymer particles or agglomerated superabsorbent polymer particles with very irregular shape may lead to a relatively high standard deviation. As will be understood by the skilled person, in such circumstances it may be desirable to increase the repetitions of sieving or increase the number of samples, accordingly.

Hence, the upper and lower particle size limits as used herein, given they are obtained by classification using sieving, are to be understood as follows: For upper particle size limits, the respective precursor superabsorbent polymer particles or the agglomerated superabsorbent polymer particles may comprise up to 10%, or up to 5% by weight of precursor superabsorbent polymer particles or the agglomerated superabsorbent polymer particles having a higher particle size than the upper particle size limit. For lower particle size limits, the respective precursor superabsorbent polymer particles or the agglomerated superabsorbent polymer particles may comprise up to 10%, or up to 5% by weight of precursor superabsorbent polymer particles or the agglomerated superabsorbent polymer particles having a lower particle size than the lower particle size limit.

Additionally to classifying the precursor superabsorbent polymer particles to have an upper particle size limit, it may also be desirable to further classify the precursor superabsorbent polymer particles such that they also have a lower particle limit. The lower particle size limit may be 20 µm, or 30 µm, or 45 µm, or 63 µm or 80 µm.

The difference between the upper particle size limit and the lower particle size limit of the precursor superabsorbent polymer particles provided in step a) may be less than 600 µm, or less than 500 µm, or less than 300 µm, or less than 150 µm. The difference between the upper particle size limit and the lower particle size limit may also not be less than 20 µm.

Classification can be used to obtain precursor superabsorbent polymer particles having the desired first mass average particle size $^1$mAvPS.

The precursor superabsorbent polymer particles provided may be base polymer, i.e. precursor superabsorbent polymer particles not having undergone any surface cross-linking. However, although less desirable, the precursor superabsorbent polymer particles may also be surface cross-linked and/or may have undergone other treatments, such as coating.

Generally, the precursor superabsorbent polymer particles provided under step a) are desirable dry precursor superabsorbent polymer particles having a water content of less than 10% by weight, or less than 5% by weight, or less than 3% by weight of the precursor superabsorbent polymer particles. However, the precursor superabsorbent polymer particles provided under a) may also have a higher water content, such as up to 15% by weight, up to 25% by weight, up to 50% by weight, or even higher.

b) Mixing the Precursor Superabsorbent Polymer Particles with a Solution Comprising Clay Platelets, One or More Surface Modification Compound(s) and/or Edge Modification Compound(s) and Polymerizable Monomers and/or Oligomers or Crosslinkable Polymers, The precursor superabsorbent polymer particles having a first mass average particle size $^1$mAvPS are mixed with a solution comprising clay platelets, one or more surface modification compound(s) and/or edge modification compound(s) and polymerizable monomers and/or oligomers or crosslinkable polymers.

The solution may comprise water. The solution may comprise further solvents in addition to water, such as organic solvent. However, it is desirable not to use any solvents in addition to water.

Mixing of the precursor superabsorbent polymer particles with the solution comprising clay platelets with modified surfaces and/or edges may be done at a rate of at least 1 g, or at least 2 g, or at least 4 g, or at least 6 g, or at least 8 g of solution per kg of provided precursor superabsorbent polymer particles per minute. The rate may be less than 200 g/kg/min, or less than 100 g/kg/min.

Mixing can be done by spraying the solution comprising clay platelets with modified surfaces and/or edges onto the precursor superabsorbent polymer particles. It may be desirable to agitate the precursor superabsorbent polymer particles during and/or after the solution is applied.

Mixing can be done in equipment well known in the art, such as coaters, paddle mixers, ploughshare mixers, kneaders, fluidized bed coaters, Wurster coaters, spinning disk reactors, etc.

Mixing can be done at room temperature or at elevated temperatures (e.g. around 30° C. to 100° C., more preferably around 40° C. to 70° C.). If mixing is done at elevated temperatures, the resulting agglomerated superabsorbent polymer particles may already be sufficiently dry such that no subsequent drying step is needed. However, the temperatures may not be as high as to evaporate an excessive amount of the applied solution too fast.

If the solution comprises a first type of crosslinkers, a polymerization step will be necessary. For example, the polymerization step may be a radical polymerization step.

The mixed solution comprising precursor superabsorbent polymer particles, clay platelets with modified surfaces and/or edges, polymerizable monomers and/or oligomers and a first type of crosslinkers may be polymerizable by any type of polymerization reaction, by use of a polymerization initiator system that is activated, to initiate the polymerization. The polymerization initiator system may be activated by applying heat (at a temperature of 120° C. or higher than 120° C.) and/or radiation. After the polymerization, agglomerated superabsorbent polymer particles are obtained.

If desired, polymerization step can be followed by a drying step, e.g. at temperatures of e.g. more than 50° C., more than 100° C., more than 120° C., more than 180° C. or more than 200° C. or preferably of 100° C. to 150° C.

If the solution comprises a second type of crosslinkers being amide acetals, carbamic esters, polyhydric alcohols like diols or polyols, cyclic carbonates or bisoxazolines or epoxides, a polymerization step may not be necessary. For example, a radical polymerization step may not be necessary.

If the solution comprises a second type of crosslinkers, a crosslinking step follows the mixing step.

A crosslinking step may be done with the mixed solution comprising precursor superabsorbent polymer particles, clay platelets with modified surfaces and/or edges, crosslinkable polymers and a second type of crosslinkers.

The crosslinking step may be a heating step at a temperature of 120° C. or higher than 120° C. or a drying step. After the crosslinking step, agglomerated superabsorbent polymer particles are obtained.

If desired, crosslinking step can be followed by a drying step, e.g. at temperatures of e.g. more than 50° C., more than 100° C., more than 120° C., more than 180° C. or more than 200° C. or preferably of 100° C. to 150° C.

The agglomerated superabsorbent polymer particles obtained by step b) and the optional drying step are desirably dry agglomerated superabsorbent polymer particles. The dry agglomerated superabsorbent polymer particles may have a water content of less than 10% by weight, or less than 5% by weight, or less than 3% by weight.

According to the present invention, the mass average particle size of the obtained agglomerated superabsorbent polymer particles (herein referred to as the second mass average particle size $^2$mAvPS) is at least 25% higher than the first mass average particle size $^1$mAvPS, which is the mass average particle size of the precursor superabsorbent polymer particles before having been subjected to the solution comprising clay platelets with modified surfaces and/or edges, and the polymerizable monomers and/or oligomers or crosslinkable polymers. The second mass average particle size $^2$mAvPS may be at least 30%, or at least 40% or at least 50% higher than the first mass average particle size $^1$mAvPS.

If the second mass average particle size $^2$mAvPS, after step b) has been carried out, is less than 25% higher than the first mass average particle size $^1$mAvPS, a classification step can be added after step b).

By this classification step, the amount of non-agglomerated superabsorbent polymer particles can be significantly reduced such that the second mass average particle size $^2$mAvPS increases.

The optional classification step carried out after step b), and after the optional drying step eliminates precursor superabsorbent polymer particles with a particle size below a lower particle size limit. The lower particle size limit of the optional classification step and hence, of the agglomerated superabsorbent polymer particles may be 150 μm, or may be 300 μm, or may be 500 μm.

If the precursor superabsorbent polymer particles having the first mass average particle size $^1$mAvPS have been provided by a classification step and have an upper particle size limit, the lower particle size limit of the optional classification step carried out after step b) (and after the optional drying step), the lower particle size limit of the classification step on the agglomerated superabsorbent polymer particles may be from 80% to 100%, or from 90% to 100% of the upper particle size limit of the precursor superabsorbent polymer particles having a first mass average particle size $^1$mAvPS. Hence, in this latter classification step, the majority (or substantially all, if the lower particle size limit of the agglomerates is 100% of—i.e. equal to—the upper particle size of the particles with the first average particle size) of non-agglomerated superabsorbent polymer particles will be sieved out and the agglomerated superabsorbent polymer particles are retained.

If the agglomerated superabsorbent polymer particles of the present invention are formed with base polymer particles, i.e. with precursor superabsorbent polymer particles not having undergone any surface cross-linking prior to agglomerate formation, the base polymer made can be obtained as follows:

Providing a polyacrylic acid polymer gel. The polyacrylic acid polymer gel may be made by well known methods, and may e.g. be made by polymerizing acrylic acid monomers, e.g. by polymerizing the acrylic acid monomers at 50% to 95% neutralization. Neutralization is typically done with sodium hydroxide.

The gel is submitted to a first grinding step followed by a first drying step to obtain base polymer particles, If, after the first drying step, the base polymer particles are too dry for the second grinding step, the base polymer particles can optionally be rewetted.

Subsequently, the base polymer particles may be subjected to a second grinding step followed by a second drying step.

Alternatively, no grinding step may be necessary. For example, the base polymer particles may be obtained according to the method described in WO2015014826A1 of BASF SE, WO2012066888A1 of SUMITOMO or in WO2015062883 of BASF SE.

Before being submitted to the second grinding step, the water content of the base polymer particles may be at least 0.4 g water per g of dry base polymer particles, but may be not more than 15 g/g, desirably from 0.4 g/g to 5 g/g, or from 0.8 g/g to 3 g/g, or from 1 g/g to 2 g/g. The respective water content can be obtained by either drying the base polymer particles in the first drying step to the desired water content level (i.e. not "completely" drying the base polymer particles). Alternatively, if the base polymer particles derived after the first drying step are too dry, they can be rewetted to obtain the desired water content prior to the second grinding step.

By providing a first and a second grinding step, it is possible to obtain base polymer particles having a relatively high surface area as the polymer has been exposed to the shear forces in the grinder two times.

Surface Cross-Linking

Surface cross-linking of superabsorbent polymer particles is well known in the art.

The agglomerated superabsorbent polymer particles may be surface crosslinked. For the present invention, surface cross-linking of the agglomerated superabsorbent polymer particles or, though less desirable, surface cross-linking of the precursor superabsorbent polymer particles prior to or simultaneously with the mixing step to form the agglomerates can be done by any of the known surface cross-linking methods.

Commonly applied surface cross-linkers are thermally activated surface cross-linkers. The term "thermally activated surface cross-linkers" refers to surface cross-linkers, which only react upon exposure to increased temperatures, typically around 150° C. Thermally activated surface cross-linkers known in the prior art are e.g. di- or polyfunctional agents that are capable of building additional cross-links between the polymer chains of the precursor superabsorbent polymer particles. Other thermally activated surface cross-linkers include, e.g., di- or polyhydric alcohols, or derivatives thereof, capable of forming di- or polyhydric alcohols. Representatives of such agents are alkylene carbonates, ketales, and di- or polyglycidlyethers. Moreover, (poly) glycidyl ethers, haloepoxy compounds, polyaldehydes, polyoles and polyamines are also well known thermally activated surface cross-linkers. The cross-linking is based on a reaction between the functional groups comprised by the precursor superabsorbent polymer particle, for example, an esterification reaction between a carboxyl group (comprised by the polymer) and a hydroxyl group (comprised by the surface cross-linker).

In general, the surface cross-linking agent is applied on the surface of the precursor superabsorbent polymer particles prior to, during, or, more desirable, after the agglomerated superabsorbent polymer particles are formed due to mixing the precursor superabsorbent polymer particles with the solution comprising clay platelets with modified surfaces and/or edges and the polymerizable monomers and/or oligomers or crosslinkable polymers. Therefore, the reaction preferably takes place on the surface of the precursor superabsorbent polymer particles or of the agglomerated superabsorbent polymer particles, which results in improved cross-linking on the surface of the particles while not substantially affecting the core of the particles. Thereby, the surface of the (agglomerated) (precursor) superabsorbent polymer particles becomes stiffer.

Surface cross-linking agents are often applied in a solution which consists of, or comprises an organic solvent. Such organic solvent generally renders the surface of the precursor superabsorbent polymer particles less sticky compared to the use of water as solvent. However, for forming agglomerated superabsorbent polymer particles, a sticky surface is desirable as it fosters agglomeration. Hence, especially if the surface cross-linkers are applied in a solution consisting of or comprising an organic solvent, it may be desirable to surface cross-link the precursor superabsorbent polymer particles after the agglomerated superabsorbent polymer particles are formed due to mixing the precursor superabsorbent polymer particles with the solution comprising clay platelets with modified surfaces and/or edges and the polymerizable monomers and/or oligomers or crosslinkable polymers.

However, the surface cross-linker can also be added in an aqueous solution, via gas phase (i.e. vaporizing a liquid surface cross-linker) or by adding a pure surface cross-linker in liquid form.

The surface cross-linker may also be added together with other substances, such as surfactants.

Typically, surface cross-linking will be done at temperatures of at least 100° C., or at least 120° C., or at least 150° C. It may be desirable to not increase the temperature above 200° C., or not above 180° C. to avoid e.g. yellowing of the (agglomerated) (precursor) superabsorbent polymer particles.

Absorbent Articles

A typical disposable absorbent article, in which the agglomerated superabsorbent polymer particles of the present invention can be used, is placed against or in proximity to the body of the wearer to absorb and contain the various exudates discharged from the body and is represented in FIG. 1 to FIG. 5 in the form of a diaper 20.

In more details, FIG. 1 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

Figure 2:
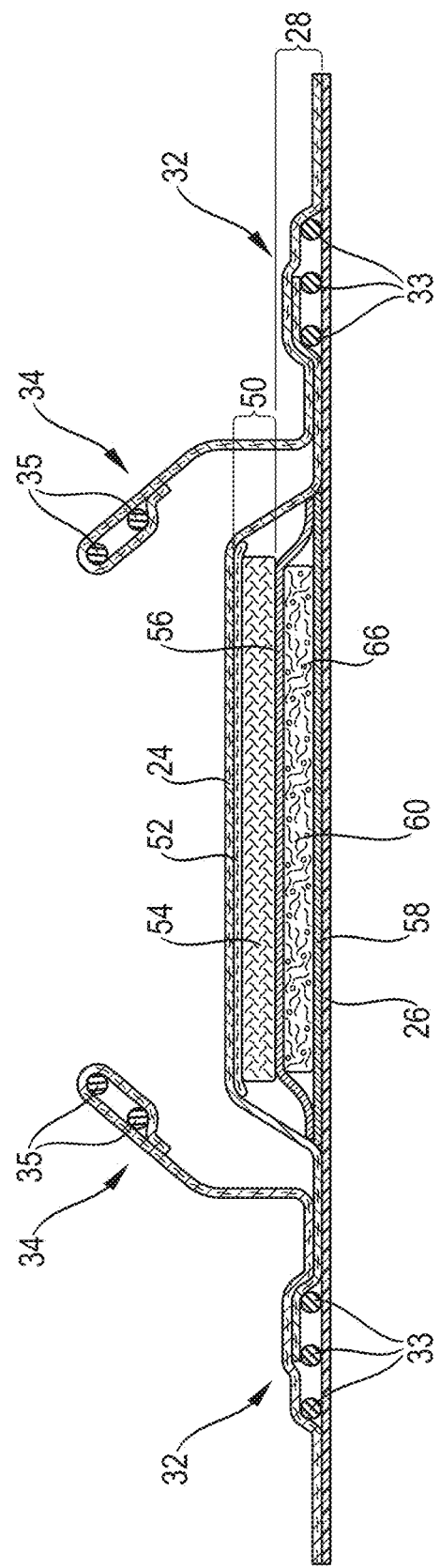
FIG. 2 is a transversal cross-section of the diaper of FIG. 1.

As shown in FIGS. 1 and 2, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as the agglomerated superabsorbent polymer particles of the present invention 66 and/or cellulose fibers, as well as other absorbent and non-absorbent materials commonly used in absorbent articles (e.g. thermoplastic adhesives immobilizing the superabsorbent polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), superabsorbent polymer particles disposed on the one or more substrate layers, and a thermoplastic composition typically disposed on the superabsorbent polymer particles. Typically the thermoplastic composition is a thermoplastic adhesive material. In one embodiment, the thermoplastic adhesive material forms a fibrous layer which is at least partially in contact with the superabsorbent polymer particles on the one or more substrate layers and partially in contact with the one or more substrate layers. Auxiliary adhesive might be deposited on the one or more substrate layers before application of the superabsorbent polymer particles for enhancing adhesion of the superabsorbent polymer particles and/or of the thermoplastic adhesive material to the respective substrate layer(s). The absorbent core may also include one or more cover layer(s) such that the superabsorbent polymer particles are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the superabsorbent polymer particles, the thermoplastic composition, optionally the auxiliary adhesive, optionally the cover layer(s), and optionally odor control compounds.

The absorbent core may also comprise a mixture of superabsorbent polymer particles and airfelt, which may be enwrapped within one or more substrate layers, such as nonwoven webs or paper tissue. Such absorbent cores may comprise from 30% to 95%, or from 50% to 95% of superabsorbent polymer particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of superabsorbent polymer particles by weight of the absorbent material.

The absorbent core may comprise mixtures of the agglomerated superabsorbent polymer particles of the present invention and other superabsorbent polymer particles. For example, the absorbent core may comprise at least 70%, or at least 80%, or at least 90% or 100% of superabsorbent polymer particles by weight of the absorbent material, wherein the superabsorbent polymer particles comprise at least 10%, or at least 20% or at least 30% or at least 50% by weight of the agglomerated superabsorbent polymer particles.

The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers.

The ADS may be free of superabsorbent polymer. The prior art discloses many types of acquisition-distribution systems, see for example WO2000/59430, WO95/10996, U.S. Pat. No. 5,700,254, WO02/067809. However, the agglomerated superabsorbent polymer particles of the present invention may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m², in particular from 80 to 300 g/m².

The distribution layer may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a non-woven material, for example a SMS or SMMS material, comprising a spunbonded, a melt-blown and a further spun-bonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13 to 15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 1 and 2. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Area(s) 29 Substantially Free of Absorbent Material and Channels 29'

Figure 3:
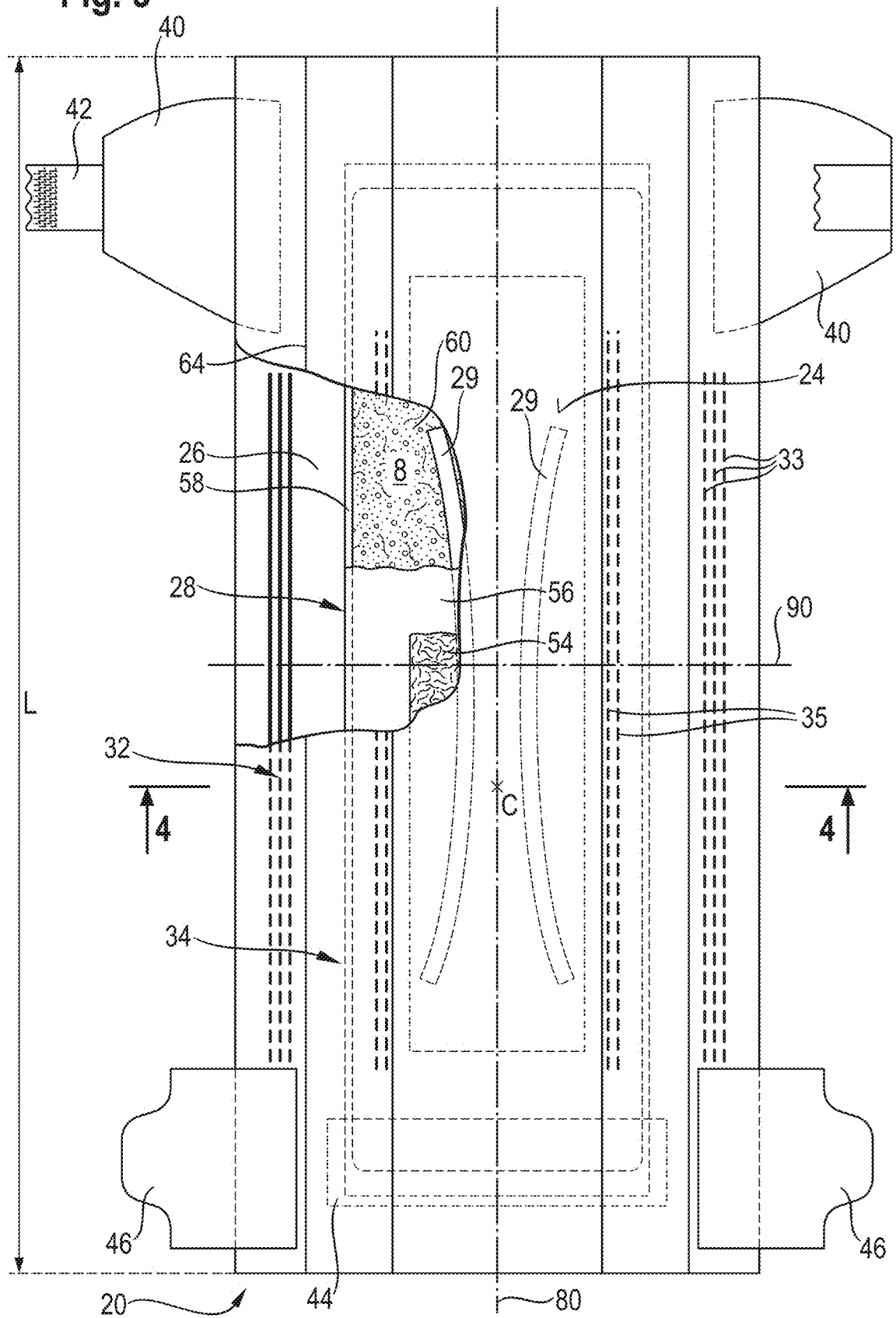
FIG. 3 is a top view of an exemplary absorbent article in the form of a diaper which may comprise the agglomerated superabsorbent polymer particles of the present invention, with area(s) substantially free of absorbent material.

As shown in FIG. 3, the absorbent core 28 may comprise one or more area(s) 29 which is/are substantially free of absorbent material. By "substantially free" it is meant that in each of these areas the basis weight of the absorbent material is less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The areas 29 are advantageously surrounded by the absorbent material, when seen in the plane of the core, which means that the area(s) 29 does not extend to any of the edge of the deposition area 8 of the absorbent material.

Figure 4:
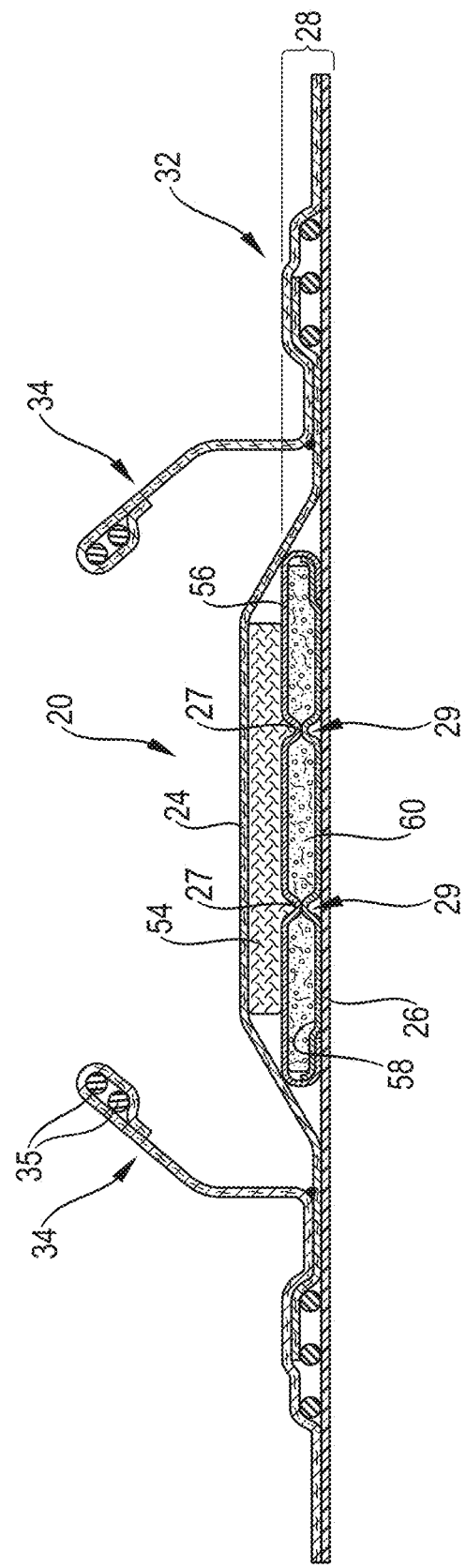
FIG. 4 is a transversal cross-section of the article of FIG. 3.
Figure 5:
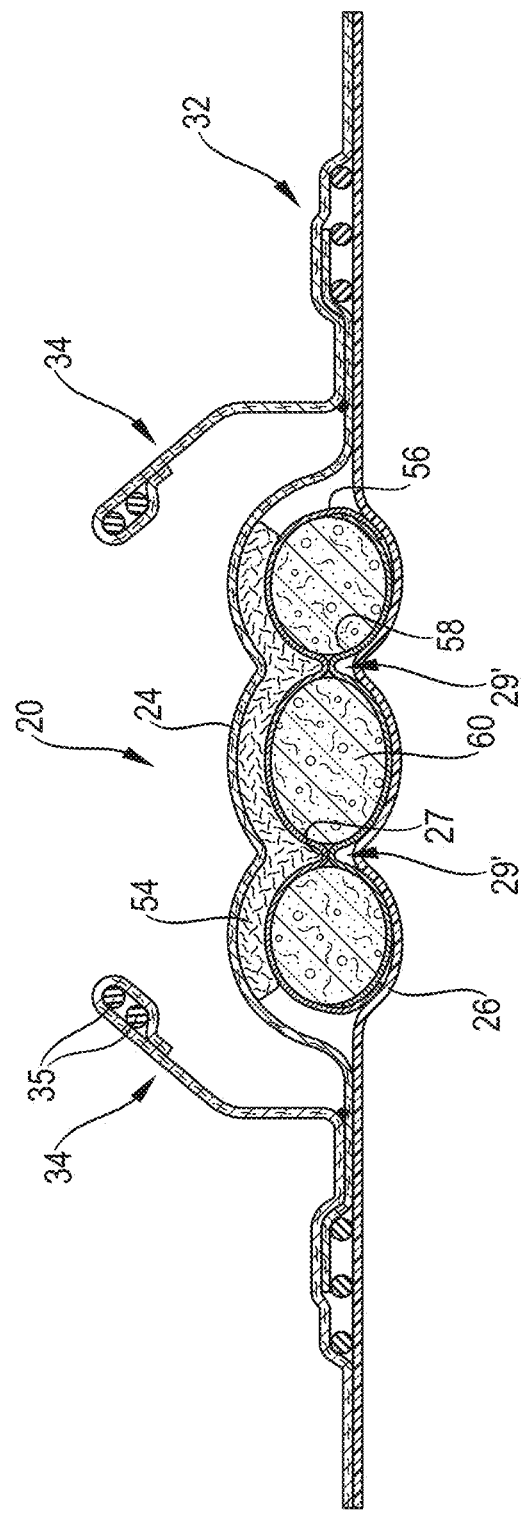
FIG. 5 is a transversal cross-section of the article taken at the same point as FIG. 4 where channels have formed in the core as a result of the diaper being loaded with fluid.

The upper core cover layer 56 is attached to the lower cover layer 58 by core wrap bond(s) 27 through these area(s) 29 substantially free of absorbent material. As shown in FIG. 4 and FIG. 5, when the absorbent material swells upon absorbing a liquid, the core wrap bond remains at least initially attached in the substantially material free area(s) 29. The absorbent material swells in the rest of the core when it absorbs a liquid, so that the core wrap forms one or more channel(s) 29' along the area(s) 29 substantially free of absorbent material comprising the core wrap bond 27. These channels 29' are three dimensional and can serve to distribute an insulting fluid along their length to a wider area of the core. This may provide a quicker fluid acquisition speed and a better utilization of the absorbent capacity of the core. The channels 29' can also provide a deformation of an overlying layer such as a fibrous layer 54 and provide corresponding ditches 29 in the overlying layer. It is not excluded that the absorbent core may comprise other area(s) substantially free of absorbent material but without a core wrap bond, but these non-bonded areas will typically not form a channel when wet.

The upper core cover layer 56 and the lower cover layer 58 may be attached together continuously along the area(s) 29 substantially free of absorbent material, but the core wrap bond 27 may also be discontinuous (intermittent) such as series of point bonds. Typically, an adhesive can be used to attach the top side to the bottom of the core wrap, but it is possible to bond via other known attachment means, such as pressure bonding, ultrasonic bonding or heat bonding or combination thereof. The attachment of the top side and bottom side of the core wrap may be provided by one or more adhesive material, in particular one or more layers of auxiliary glue and/or one or more layers of fibrous adhesive material, if present in the core, as indicated below. These glues may therefore serve the dual function of immobilizing the absorbent material and attach the top side and the bottom side of the core together.

The following examples of the shape and size of the areas 29 substantially free of absorbent material are not limiting. In general, the core wrap bond 27 may have the same outline but be slightly smaller than the areas 29 due to the tolerance required in some manufacturing process. The substantially material free area(s) 29 may be present within the crotch region of the article, in particular at least at the same longitudinal level as the crotch point C, as represented in FIG. 3 by the two longitudinally extending areas substantially free of absorbent material 29. The absorbent core 28 may also comprise more than two substantially absorbent material free area(s), for example at least 3, or at least 4 or at least 5 or at least 6. The absorbent core may comprise one or more pairs of areas substantially free of absorbent material symmetrically arranged relative to the longitudinal axis 80. Shorter area(s) substantially free of absorbent material may also be present, for example in the back region or the front region of the core, as seen for example in the Figures of WO2012/170778.

The area(s) 29 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 29 substantially free of absorbent material may have a length projected on the longitudinal axis 80 of the core that is at least 10% of the length of the absorbent core, in particular from 20% to 80%. It may be advantageous that at least some or all of the area(s) 29 are not completely or substantially completely transversely oriented channels in the core.

The area(s) 29 substantially free of absorbent material may be completely oriented longitudinally and parallel to the longitudinal axis but also may be curved. In particular some or all these area(s), in particular these area(s) present in the crotch region, may be concave towards the longitudinal axis 80, as for example represented in FIG. 3 for the pair of channels 29'. The radius of curvature may typically be at least equal (and preferably at least 1.5 or at least 2.0 times this average transverse dimension) to the average transverse dimension of the absorbent material deposition area 8; and also straight but under an angle of (e.g. from 5°) up to 30°, or for example up to 20°, or up to 10° with a line parallel to the longitudinal axis. The radius of curvature may be constant for a substantially absorbent material free area(s), or may vary along its length. This may also includes area(s) substantially free of absorbent material with an angle therein, provided said angle between two parts of a channel is at least 120°, preferably at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

In some embodiments, there is no area(s) substantially free of absorbent material that coincides with the longitudinal axis 80 of the core. When present as one ore symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 8, and are therefore surrounded by and fully encompassed within the absorbent material deposition area 8 of the core. Typically, the smallest distance between an area(s) substantially free of absorbent material and the closest edge of the absorbent material deposition area is at least 5 mm.

The area(s) substantially free of absorbent material may have a width We along at least part of its length which is at least 2 mm, or at least 3 mm or at least 4 mm, up to for example 20 mm, or 16 mm or 12 mm. The width We of the area(s) substantially free of absorbent material may be constant through substantially its whole length or may vary along its length.

The channels 29' in the absorbent core start forming when the absorbent material absorbs a liquid such as urine and starts swelling. As the core absorbs more liquid, the depressions within the absorbent core formed by channels will become deeper and more apparent to the eye and the touch. It is possible to create a sufficiently strong core wrap bond combined with a relatively low amount of superabsorbent polymer particles so that the channels remain permanent until complete saturation of the absorbent material. On the other hand, the core wrap bonds may in some cases also restrict the swelling of the absorbent material when the core is substantially loaded.

Initially, the core wrap bond(s) may be designed to be closed and to increase the pressure in the areas adjacent to the core wrap bond(s). At some point, the core wrap bond (27) may also be designed to open in a controlled manner when exposed to a large amount of fluid.

Test Methods

Sieve Test to Determine Mass Average Particle Size (mAvPS):

All testing is conducted at 23±2° C. and at 45%±10 relative humidity.

10 g (+0.1 g, weighed to an accuracy of at least 0.01 g) of a representative sample of the respective precursor superabsorbent polymer particles or agglomerated superabsorbent polymer particles are sieved via sieves of about 20 cm in diameter (available e.g. from Retsch GmbH, Haan, Germany; DIN/ISO 3310-1). A stack of sieves with the following mesh sizes (sequence from top to bottom) is used: 1600 µm, 1400 µm, 1000 µm, 850 µm, 710 µm, 600 µm, 500 µm, 425 µm, 300 µm, 212 µm, 150 µm, 106 µm, 63 µm, 45 µm and pan (taken herein as equivalent to 1 µm). The weight of each empty sieve is noted down, to an accuracy of 0.01 g.

The 10 g sample is loaded to the top sieve (i.e. 1600 µm) and sieved via a sieve machine ("AS 00 control 'g'" available from Retsch GmbH, Haan, Germany) for 3 min at 1 mm/'g'. The weight of each sieve after sieving is noted down, to an accuracy of 0.01 g. The difference between the weight of loaded sieve and the empty sieve for each size gives the weight of particles per mesh size.

In case the difference between loaded and empty sieve is negative, but larger than minus 0.02 g (which might occur due to weighing accuracy to 0.01 g), the negative difference is accounted as 0.

In case the difference between loaded and empty sieve is negative and smaller than minus 0.02 g (e.g. minus 0.5 g), the results of the sieving test are discarded and the sieving test is repeated.

As size of the sieve Di the sieve notation is taken, e.g. on sieve 500 μm is the fraction with D500 to an amount of m500, with D500=500 am.

The mass average particle size (mAvPS) herein is calculated as $$mAvPS = \frac{\sum_{i} m_i \cdot D_i}{\sum_{i=top\_to\_bottom} m_i} = \frac{\sum_{i} m_i \cdot D_i}{m_{total}} \quad (I)$$

Exemplary Calculation:

TABLE 1

| Sieve Size [μm] | Fraction on Sieve [g] | Percentage |
|---|---|---|
| 1600 | 0.00 | 0.0% |
| 1400 | 0.00 | 0.0% |
| 1000 | 0.00 | 0.0% |
| 850 | 0.30 | 3.0% |
| 710 | 0.70 | 7.0% |
| 600 | 1.30 | 13.0% |
| 500 | 3.80 | 38.0% |
| 425 | 2.40 | 24.0% |
| 300 | 0.50 | 5.0% |
| 212 | 0.70 | 7.0% |
| 150 | 0.30 | 3.0% |
| 106 | 0.00 | 0.0% |
| 63 | 0.00 | 0.0% |
| 45 | 0.00 | 0.0% |
| 1 | 0.00 | 0.0% |
| Total | 10.00 | 100.0% |

In this example, mAvPS is 486 μm.

To simplify the sieving procedure, a reduced stack of sieves can be used in case particles of a certain size are not expected (e.g. if the sample was pre-sieved in the sample preparation).

E.g. for a pre-sieved sample with upper pre-sieve size of 150 μm, the following sieve stack might be used: 300 μm, 212 μm, 150 μm, 106 μm, 63 μm, 45 μm and pan (taken herein as equivalent to 1 μm).

Note: In case a reduced sieve stack is used, the top (or bottom) sieve should be loaded with not more than 5 wt % of the total sample. If loading is >5 wt %, additional sieves of appropriate size need to be included in the stack and the sieving test needs to be repeated.

E.g. for a pre-sieved sample with lower pre-sieve size of 850 μm the following sieve stack might be used: 1600 μm, 1400 μm, 1000 μm, 850 μm, 710 μm, 600 μm, 500 μm and pan (taken herein as equivalent to 1 μm).

Urine Permeability Measurement (UPM) Test Method
Lab Conditions:

This test has to be performed in a climate conditioned room at standard conditions of 23° C.±2° C. temperature and 45%±10% relative humidity.
Urine Permeability Measurement System This method determined the permeability of a swollen hydrogel layer 1318. The equipment used for this method is described below. This method is closely related to the SFC (Salt Flow Conductivity or Saline Flow Conductivity) test method of the prior art.

Figure 6:
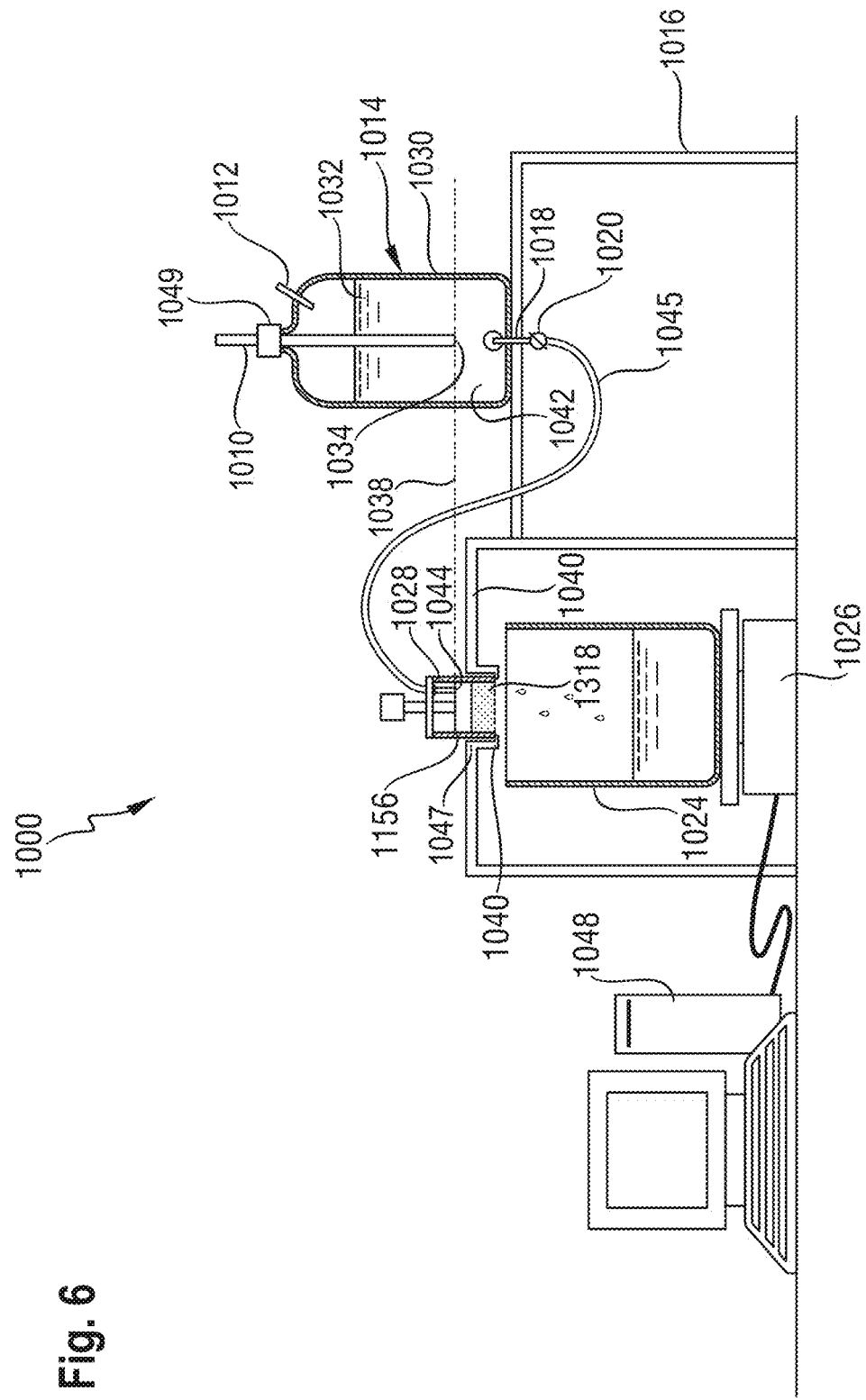
FIG. 6 is a partial cross-sectional side view of a suitable permeability measurement system for conducting the Urine Permeability Measurement Test.

FIG. 6 shows permeability measurement system 1000 set-up with the constant hydrostatic head reservoir 1014, open-ended tube for air admittance 1010, stoppered vent for refilling 1012, laboratory reck 1016, delivery tube 1018 with flexible tube 1045 with Tygon tube nozzle 1044, stopcock 1020, cover plate 1047 and supporting ring 1040, receiving vessel 1024, balance 1026 and piston/cylinder assembly 1028.

Figure 7:
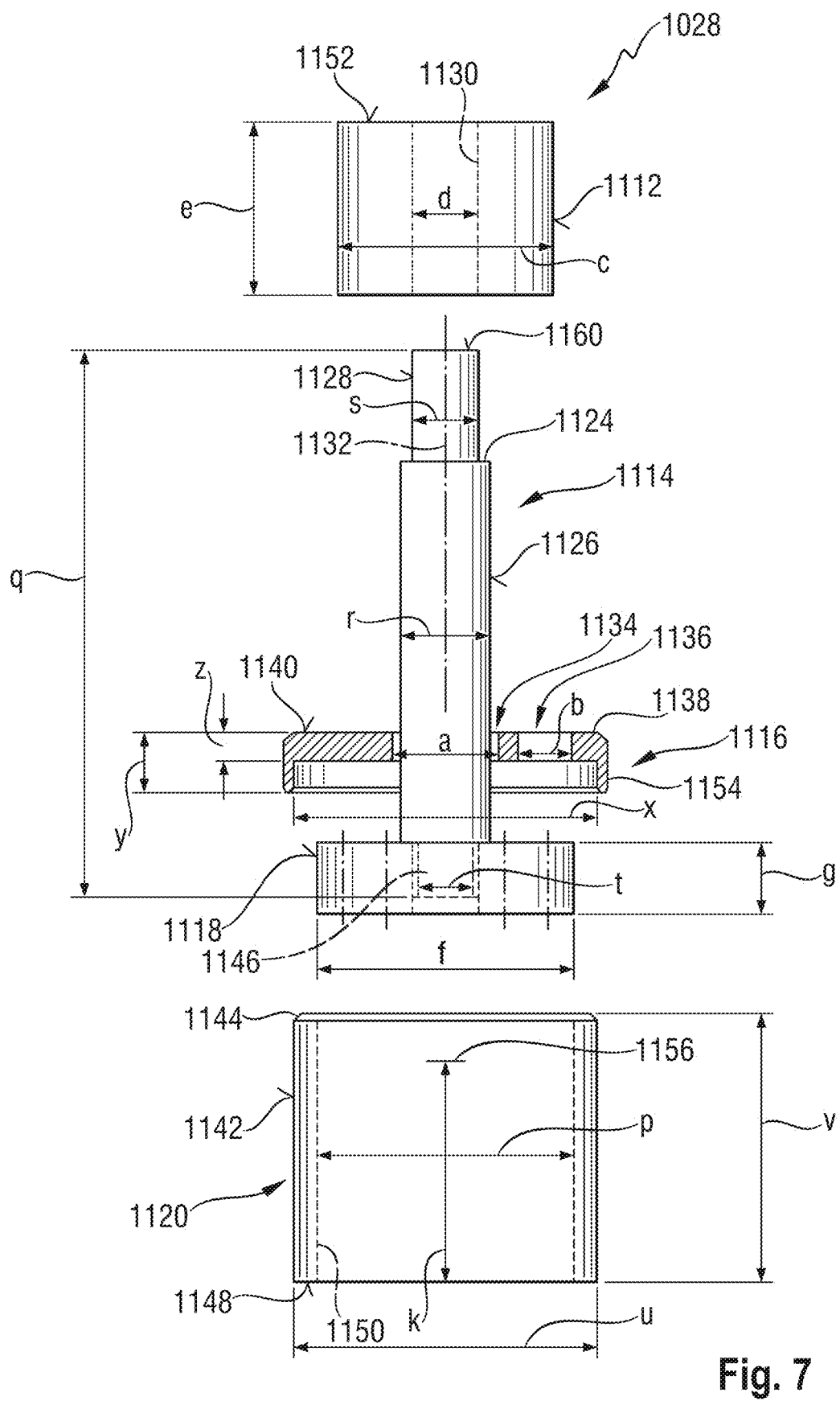
FIG. 7 is a cross-sectional side view of a piston/cylinder assembly for use in conducting the Urine Permeability Measurement Test.
Figure 8:
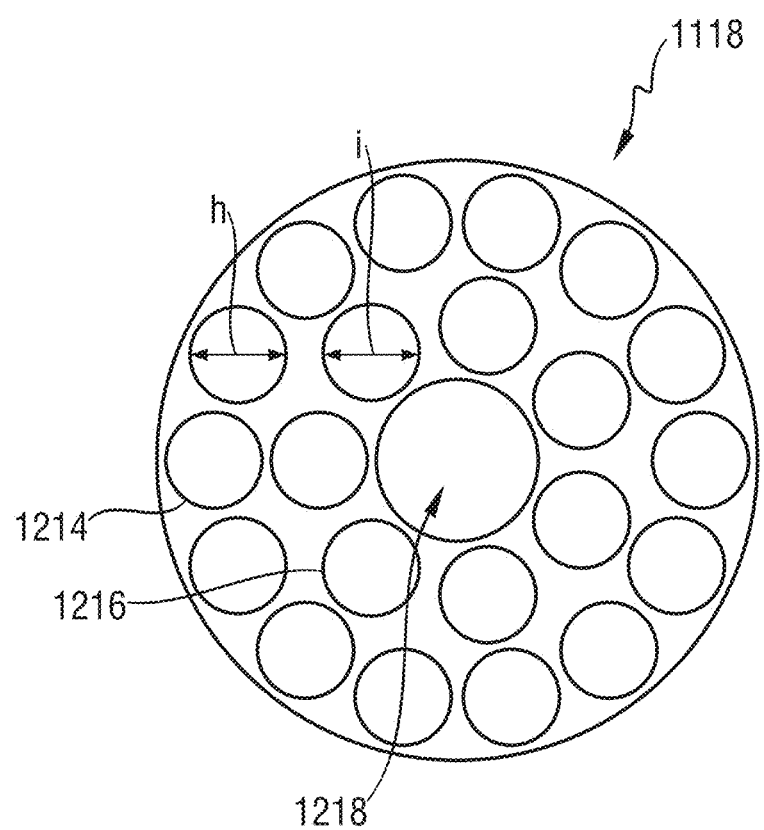
FIG. 8 is a top view of a piston head suitable for use in the piston/cylinder assembly shown in FIG. 7.

FIG. 7 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a stainless-steel screen cloth (ISO 9044 Material 1.4401, mesh size 0.038 mm, wire diameter 0.025 mm) (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 22.15 (±0.02) mm. An upper portion 1128 of the piston shaft 1114 has a diameter s of 15.8 mm, forming a shoulder 1124. A lower portion 1146 of the piston shaft 1114 has a diameter t of approximately ⅝ inch (15.9 mm) and is threaded to screw firmly into the center hole 1218 (see FIG. 8) of the piston head 1118. The piston head 1118 is perforated, made of transparent polycarbonate (e.g., Lexan®), and is also screened with a stretched stainless-steel screen cloth (ISO 9044 Material 1.4401, mesh size 0.038 mm, wire diameter 0.025 mm) (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the inner area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be repositioned with the same orientation relative to one another for each measurement.

The cylinder 1120 specification details are:
Outer diameter u of the Cylinder 1120: 70.35 mm (±0.05 mm)
Inner diameter p of the Cylinder 1120: 60.0 mm (±0.05 mm)
Height v of the Cylinder 1120: 60.5 mm. Cylinder height must not be lower than 55.0 mm!

The cylinder lid 1116 specification details are:
Outer diameter w of cylinder lid 1116: 76.05 mm (±0.05 mm)
Inner diameter x of cylinder lid 1116: 70.5 mm (±0.05 mm)
Thickness y of cylinder lid 1116 including lip 1154: 12.7 mm
Thickness z of cylinder lid 1116 without lip 1154: 6.35 mm
Diameter a of first lid opening 1134: 22.25 mm (±0.02 mm)
Diameter b of second lid opening 1136: 12.7 mm (±0.1 mm)
Distance between centers of first and second lid openings 1134 and 1136: 23.5 mm The weight 1112 specification details are:
Outer diameter c: 50.0 mm
Diameter d of center bore 1130: 16.0 mm
Height e: 39.0 mm The piston head 1118 specification details are:
Diameter f: 59.7 mm (±0.05 mm)
Height g: 16.5 mm. Piston head height must not be less than 15.0 mm.
Outer holes 1214 (14 total) with a 9.30 (±0.25) mm diameter h, outer holes 1214 equally spaced with centers being 23.9 mm from the center of center hole 1218.
Inner holes 1216 (7 total) with a 9.30 (±0.25) mm diameter i, inner holes 1216 equally spaced with centers being 13.4 mm from the center of center hole 1218.
Center hole 1218 has a diameter j of approximately ⅝ inches (15.9 mm) and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the cover plate 1047 and supporting ring 1040 (with circular inner opening of not less than 64 mm diameter) above the receiving vessel 1024.

The cover plate 1047 and supporting ring 1040 are parts as used in the equipment used for the method "K(t) Test Method (Dynamic Effective Permeability and Uptake Kinetics Measurement Test 5 method)" as described in EP 2 535 027 A1 and is called "Zeitabhängiger Durchlässigkeitsprüfstand" or "Time Dependent Permeability Tester", Equipment No. 03-080578 and is commercially available at BRAUN GmbH, Frankfurter Str. 145, 61476 Kronberg, Germany. Upon request, detailed technical drawings are also available.

Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 connected to a flexible tube 1045 (e.g. Tygon tube, capable to connect nozzle and reservoir outlet) and to a Tygon tube nozzle 1044 (inner diameter at least 6.0 mm, length appr. 5.0 cm) for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of approximately 12 mm, but not less than 10.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery flexible tube 1045 is dimensioned (e.g. outer diameter 10 mm) to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar 1049. The constant hydrostatic head reservoir 1014 can be positioned on a laboratory reck 1016 at a suitable height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 2.6 g/sec for at least 10 minutes.

The piston/cylinder assembly 1028 is positioned on the supporting ring 1040 in the cover plate 1047 or suitable alternative rigid stand. The salt solution 1032 passing through the piston/cylinder assembly 1028 containing the swollen hydrogel layer 1318 is collected in a receiving vessel 1024, positioned below (but not in contact with) the piston/cylinder assembly 1028.

The receiving vessel 1024 is positioned on the balance 1026 which is accurate to at least 0.001 g. The digital output of the balance 1026 is connected to a computerized data acquisition system 1048.

Preparation of Reagents (not Illustrated)

Figure 9:
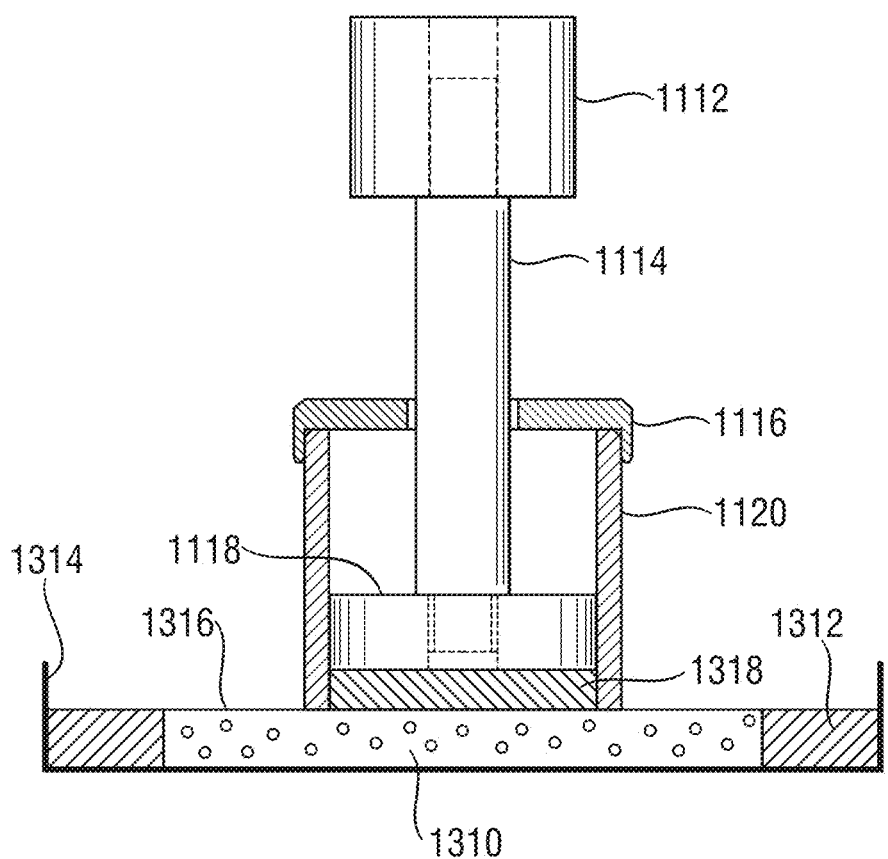
FIG. 9 is a cross-sectional side view of the piston/cylinder assembly of FIG. 7 placed on fritted disc for the swelling phase.

Jayco Synthetic Urine (JSU) 1312 (see FIG. 9) is used for a swelling phase (see UPM Procedure below) and 0.118 M Sodium Chloride (NaCl) Solution 1032 is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within +0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate (Na2SO4) 2.00 g
Ammonium dihydrogen phosphate (NH4H2PO4) 0.85 g
Ammonium phosphate, dibasic ((NH4)2HPO4) 0.15 g
Calcium chloride (CaCl2) 0.19 g—[or hydrated calcium chloride (CaCl2.2H2O) 0.25 g]
Magnesium chloride (MgCl2) 0.23 g—[or hydrated magnesium chloride (MgCl2.6H2O) 0.50 g]

To make the preparation faster, potassium chloride, sodium sulfate, ammonium dihydrogen phosphate, ammonium phosphate (dibasic) and magnesium chloride (or hydrated magnesium chloride) are combined and dissolved in the 80% of distilled water in the 1 L volumetric flask. Calcium chloride (or hydrated calcium chloride) is dissolved separately in approximately 50 ml distilled water (e.g. in a glass beaker) and the calcium chloride solution is transferred to the 1 L volumetric flask after the other salts are completely dissolved therein. Afterwards, distilled water is added to 1 L (1000 ml±0.4 ml) and the solution is stirred for a few minutes more. Jayco synthetic urine may be stored in a clean plastic container for 10 days. The solution should not be used if it becomes cloudy.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask (1000 ml±0.4 ml); and the flask is filled to volume with distilled water. A stir bar is added and the solution is mixed on a stirring plate until all the solids are dissolved.

The conductivity of the prepared Jayco solution must be in the range of appr. 7.48-7.72 mS/cm and of the prepared 0.118 M Sodium Chloride (NaCl) Solution in the range of appr. 12.34-12.66 mS/cm (e.g. measured via COND 70 INSTRUMENT without CELL, #50010522, equipped with Cell VPT51-01 C=0.1 from xs instruments or via LF 320/Set, #300243 equipped with TetraCon 325 from WTW or COND 330i, #02420059 equipped with TetraCon 325 from WTW). The surface tension of each of the solutions must be in the range of 71-75 mN/m (e.g. measured via tensiometer K100 from Kruess with Pt plate).

Test Preparation

Using a solid reference cylinder weight (not shown) (50 mm diameter; 128 mm height), a caliper gauge (not shown) (measurement range 25 mm, accurate to 0.01 mm, piston pressure max. 50 g; e.g. Mitutoyo Digimatic Height Gage) is set to read zero. This operation is conveniently performed on a smooth and level bench (not shown) of at least approximately 11.5 cm×15 cm. The piston/cylinder assembly 1028 without superabsorbent polymer particles is positioned under the caliper gauge (not shown) and a reading, L1, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system 1048. The cover plate 1047 with the supporting ring 1040 is positioned above the receiving vessel 1024.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method NWSP 230.0.R2 (15) or via a Moisture Analyzer (HX204 from Mettler Toledo, drying temperature 130° C., starting superabsorber weight 3.0 g (±0.5 g), stop criterion 1 mg/140 s). If the moisture content of the superabsorbent polymer particles is greater than 3 wt %, then the superabsorbent polymer particles are dried to a moisture level of <3 wt %, e.g. in an oven at 105° C. for 3 h or e.g. at 120° C. for 2 h. Agglomerated superabsorbent polymer particles are dried if moisture level is greater than 5 wt %, e.g. in an oven at 105° C. for 3 h or e.g. at 120° C. for 2 h.

The empty cylinder 1120 is placed on a level benchtop 1046 (not shown) and the superabsorbent polymer particles are quantitatively transferred into the cylinder 1120. The superabsorbent polymer particles are evenly dispersed on the screen (not shown) attached to the bottom 1148 of the cylinder 1120 while rotating the cylinder 1120, e.g. aided by a (manual or electrical) turn table (e.g. petriturn-E or petriturn-M from Schuett). It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The weight 1112 is positioned on the upper portion 1128 of the piston shaft 1114 so that it rests on the shoulder 1124 such that the first and second linear index marks are aligned. The lid 1116 and piston shaft 1126 are then carefully rotated so as to align the third, fourth, fifth, and sixth linear index marks are then aligned with the first and the second linear index marks. The piston head 1118 (via the piston shaft 1114) is then gently lowered to rest on the dry superabsorbent polymer particles. Proper seating of the lid 1116 prevents binding and assures an even distribution of the weight on the hydrogel layer 1318.

Swelling Phase:

A fritted disc of at least 8 cm diameter (e.g. 8-9 cm diameter) and at least 5.0 mm thickness (e.g. 5-7 mm thickness) with porosity "coarse" or "extra coarse" (e.g. Chemglass Inc. # CG 201-51, coarse porosity; or e.g. Robu 1680 with porosity 0) 1310 is placed in a wide flat-bottomed Petri dish 1314 and JSU 1312 is added by pouring JSU 1312 onto the center of the fritted disc 1310 until JSU 1312 reaches the top surface 1316 of the fritted disc 1310. The JSU height must not exceed the height of the fritted disc 1310. It is important to avoid any air or gas bubbles entrapped in or underneath the fritted disc 1310.

The entire piston/cylinder assembly 1028 is lifted and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to ensure the hydrogel layer 1318 does not lose JSU 1312 or take in air during this procedure. The piston/cylinder assembly 1028 is placed under the caliper gauge (not shown) and a reading, L2, is recorded to the nearest 0.01 mm. If the reading changes with time, only the initial value is recorded. The thickness of the hydrogel layer 1318, L0 is determined from L2−L1 to the nearest 0.1 mm.

The piston/cylinder assembly 1028 is transferred to the supporting ring 1040 in the cover plate 1047. The constant hydrostatic head reservoir 1014 is positioned such that the delivery tube nozzle 1044 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer 1048 attached to the balance 1026, the quantity g (in g to accuracy of 0.001 g) of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation.

For each time period of 20 seconds (time $t_{(i-1)}$ to $t_i$) after the initial 60 seconds of the experiment, the respective flow rate $Fs_{(t)}$ (in g/s) and the respective mid-point of the time $t_{(1/2)t}$ (in s) is calculated according to the following formulas:

$$Fs_{(t)} = \frac{(g_{(i-1)} - g_{(i)})}{(t_{(i-1)} - t_{(i)})} \text{ and } t_{(1/2)t} = \frac{(t_{(i-1)} + t_{(i)})}{2} \quad (II)$$

The flow rate $Fs_{(t)}$ of each time interval ($t_{(i-1)}$ to $t_i$) is plotted versus the mid-point of the time $t_{(1/2)t}$ of the time interval ($t_{(i-1)}$ to $t_i$). The intercept is calculated as Fs(t=0).

Calculation of the Intercept:

The intercept is calculated via a best-fit regression line, e.g. as following: the equation for the intercept of the regression line, a, is:

$$a = y_{AVG} - b \cdot x_{AVG} \quad (III)$$

where the slope, b, is calculated as:

$$b = \frac{\Sigma(x - x_{ACG}) \cdot (y - y_{AVG})}{\Sigma(x - x_{AVG})^2} \quad (IV)$$

and where $x_{AVG}$ and $y_{AVG}$ are the sample means AVERAGE of the known_x's and AVERAGE of the known_y's, respectively.

Calculation of Urine Permeability Measurement Q:

The intercept Fs(t=0) is used to calculate Q according to the following formula:

$$Q = \frac{F_s(t=0) \cdot L_0}{\rho \cdot A \cdot \Delta P} \quad (V)$$

where the flow rate Fs(t=0) is given in g/s, $L_0$ is the initial thickness of the hydrogel layer 1318 in cm, ρ is the density of the salt solution 1032 in g/cm$^3$ (e.g. 1.003 g/cm$^3$ at room temperature). A (from the equation above) is the area of the hydrogel layer 1318 in cm$^2$ (e.g. 28.27 cm$^2$), ΔP is the hydrostatic pressure in dyne/cm$^2$ (e.g. 4920 dyne/cm$^2$), and the Urine Permeability Measurement, Q, is in units of cm$^3$ sec/g. The average of three determinations should be reported.

TABLE 2

| Variable | Description | Unit |
|---|---|---|
| $g_i$ | Mass of salt solution 1032 flown through the swollen gel layer (recorded by the balance) at the time $t_i$ (accuracy 0.001 g) | g |
| $t_i$ | Time point (every 20 s) | s |
| $t_{(1/2)t}$ | Mid-point of time for the respective time interval $t_{i-1}$ to $t_i$ | s |
| $Fs_t$ | Flow Rate at the time interval $t_{i-1}$ to $t_i$ | g/s |
| Fs (t = 0) | Intercept flow rate at t = 0 s from the plot of the flow rate Fs(t) vs. the mid-point of time $t_{(1/2)t}$. | g/s |
| $L_0$ | Thickness of the swollen gel layer (swollen with JSU 1312) before the salt solution 1032 flows through the gel layer. | cm |
| ρ | Density of the salt solution 1032 (1.003 g/cm$^3$) | g/cm$^3$ |
| A | Area of the swollen gel layer (28.27 cm$^2$) | cm$^2$ |
| ΔP | Hydrostatic pressure across the gel layer (4920 dyne/cm$^2$) | dyne/cm$^2$ |
| Q | Urine Permeability Measurement | cm$^3$ * sec/g |

Free-Swell Rate (FSR) Test Method

This method determines the speed of superabsorbent polymer particles (such as the agglomerated superabsorbent polymer particles of this invention), especially polymeric hydrogelling particles, such as cross-linked poly-acrylates to swell in 0.9% Saline (aqueous 0.9 mass % NaCl solution). The measurement principle is to allow superabsorbent polymer particles to absorb a known amount of fluid, and the time taken to absorb the fluid is measured. The result is then expressed in grams of absorbed fluid per gram of material per second. All testing is conducted at 23±2° C. and at 45%±10 relative humidity.

In case the moisture level of the sample of the superabsorbent polymer particles is more than 5% by weight, the sample is dried, e.g. in an oven at 105° C. for 3 h or at 120° C. for 2 h 20 min. Drying temperatures must not be higher than 180° C., preferably not higher than 150° C.

About 1 g (+/−0.1 g) of the test specimen is weighed to an accuracy of 0.001 g into a 25 ml beaker, which has 32 to 34 mm inside diameter, and 50 mm height. The material is evenly spread over the bottom. 20 g of 0.9% Saline are weighed to an accuracy of +/−0.01 g in a 50 ml beaker, and are then poured carefully but quickly into the beaker containing the test material. A timer is started immediately upon the liquid contacting the material. The beaker is not moved or agitated during swelling.

The timer is stopped, and the time recorded to the nearest second (or more accurately if appropriate), when the last part of undisturbed fluid is reached by the swelling particles. In order to increase the reproducibility of the determination of the end point, the liquid surface can be illuminated by a small lamp without heating the surface by that lamp. The beaker that previously contained the saline is re-weighed to determine the actually picked up liquid to within ±0.1 g.

The Free-Swell Rate is calculated as presented in the equation below by dividing the mass of absorbed liquid by the mass of superabsorbent polymer particles divided by the time and is expressed in "g/g/s".

$$FSR[g/g/s] = \frac{mass(liquid\_absorbed)[g]}{mass(superabsorber, dry)[g] \cdot time(pickup)[s]} \quad (VI)$$

The Free-Swell Rate is calculated and averaged to obtain the FSR value in g/g/s, reported to an accuracy of 0.01 g/g/s.

Examples

The following are non-limiting examples of the agglomerated superabsorbent polymer particles of the present invention. The examples are given solely for the purpose of illustration and are not to be construed as limitations of the present invention, as many variations thereof are possible without departing from the spirit and scope of the invention, which would be recognized by one of ordinary skill in the art.

Preparation of Deionized Water (>5 MΩ Cm at 25° C.) and Ice Made from Deionized Water Quality check: A sample of about 100 g of the ice is melted in a beaker (e.g. 250 ml glass beaker from VWR, LENZ07001049) and the conductivity is measured (e.g. via COND 70 INSTRUMENT without CELL, #50010522 equipped with Cell VPT51-01 C=0.1 from xs instruments or via LF 320/Set, #300243 equipped with TetraCon 325 from WTW). The conductivity has to be less than 1.6 µS/cm at 0° C.

Preparation of the clay platelets (Montmorillonite) suspension in deionized water (solid content represent about 10 wt %):

a) Purification:

Montmorillonite PGV® powder (by Nanocor) is suspended in deionized water to form a suspension (PGV at 5 wt %) and magnetically stirred at e.g. 250-600 RPM until no clumps are left and a visually homogeneous suspension is obtained. $Na_4EDTA$ is added in portions to a final concentration of 0.1 M of $Na_4EDTA$ in the suspension. The clay suspension is then stirred at about 55° C. for two hours, e.g. via a magnetic stir barr at e.g. 250-600 RPM. In order to remove the formed EDTA-metal complexes and excessive EDTA salt, the suspension is dialyzed against deionized water. The progress of the dialysis is controlled by measuring the conductivity of the deionized water (using a typical conductometer, e.g. COND 70 INSTRUMENT without CELL, equipped with Cell VPT51-01 C=0.1 from xs instruments or via LF 320/Set, equipped with TetraCon 325 from WTW). The dialysis is ended when the conductivity decreased below 30 S/cm. Fresh $Na_4EDTA$ (in amount to achieve 0.1 M of $Na_4EDTA$ in the suspension) is added and the pH of the mixture is adjusted to pH=8 at room temperature by dropwise addition of 0.01 M HCl (aqueous solution, e.g. from Sigma Aldrich, CAS #7647-01-0). The clay suspension is stirred at about 55° C. for two hours, e.g. via a magnetic stir barr at e.g. 250-600 RPM. The dialysis is conducted again as above and ended when the conductivity decreased below 30 S/cm.

Sodium citrate (CAS #6132-04-3, e.g. from Sigma-Aldrich, for molecular biology, #71402) is added as solid to the Montmorillonite PGV® suspension (to a final concentration in the mixture of 0.3 M in citrate). The suspension is buffered with 5 ml 1M sodium bicarbonate (e.g. aqueous solution, CAS #144-55-8, e.g. from Sigma-Aldrich, for molecular biology, # S5761) per 40 ml 0.3 M citrate solution. The suspension is heated to 80° C. 1 g sodium dithionite (CAS #7775-14-6) per g PGV is added and the suspension is stirred at 80° C. for one hour, e.g. via a magnetic stir barr at e.g. 250-600 RPM. The color of the suspended clay changed from beige to green. After cooling the suspension to room temperature, sodium chloride (CAS #7647-14-5, e.g. from Sigma-Aldrich, for molecular biology, # S3014) is added to provoke flocculation of the clay. Flocculation allows centrifugation of the clay. Therefore, centrifugation is carried out at 3700 RPM for ten minutes with e.g. the device Multifuge 1 L (from Heraeus). The clay dispersion is washed once via centrifugation to remove most part of the unreacted dithionite. After centrifugation, the dispersion is dialyzed again as described above in deionized water in order to remove the citrate complex and excessive citrate and dithionite, until the conductivity decreased below 30 S/cm.

The Montmorillonite PGV® suspension is purged with ozone produced by an ozonizer (e.g. OZON/Ozon Generator 500 from Fischer) for three days.

b) Concentration:

The purified Montmorillonite PGV® suspension (after the last step, the concentration is about 2 wt % of PGV) is concentrated to up to 7 wt %. by rotation evaporation (Heidolph, Type Hei-VAP Value equipped with a Vacuubrand pump (Vacuubrand GmbH, Germany), type PC 5/MZ 2C) at 45° C. and 60 mbar reduced pressure. Further, concentration to 10 wt %. clay content is accomplished by simple evaporation in a drying cabinet (Memmert, Type UNE 400) at temperatures of about 30-45° C. for as needed time (for 10 wt % typically 24 hours).

Preparation of the Precursor Superabsorbent Polymer Particles (Base Polymer):

A 20 000 ml resin kettle (equipped with a four-necked glass cover closed with septa, suited for the introduction of a thermometer and syringe needles) is charged with about 3609.2 g of ice (ice prepared from deionized water representing about 30-40% of the total amount of ice, which is 12639.1 g). A magnetic stirrer, capable of mixing the whole content (when liquid), is added and stirring is started (e.g. elliptic magnetic stir barr from VWR, #442-0507). Stirring can take place e.g. at 250-600 RPM.

35.1 g of deionized water is taken to dissolve 4.514 g of "V50" (=2,2'-azobis (N,N'-dimethyleneisobutyramidine) dihydrochloride, from Wako Chemicals GmbH, CAS #2997-92-4) e.g. in a glass vessel with plastic snap-on cap (e.g. from VWR, #216-1777). The vessel with the "V50" solution is closed and set aside in a fridge at about 4° C.

200.0 g of glacial acrylic acid (AA, CAS #79-10-7; Acrylic Acid for synthesis, e.g. from Merck, #800181) is taken from the total amount of 4000.1 g AA to dissolve 25.60 g of MBAA (N,N'-Methylenebisacrylamide, CAS #110-26-9, for electrophoresis, from Sigma-Aldrich Chemie GmbH, # M7279) in a beaker (e.g. 400 ml glass beaker from VWR, #213-1108). The beaker with the MBAA solution is covered e.g. with parafilm (e.g. Parafilm Laboratory Film from Bemis Flexible Packaging) and set aside.

The remaining AA is added to the ice in the resin kettle while stirring is continued.

A thermometer is introduced into the resin kettle and in total 3330.7 g of 50 w % NaOH solution (for analysis, from Merck, #158793, CAS #1310-73-2) and the remaining amount of ice (prepared from deionized water) are added subsequently in portions such that the temperature is in the range of about 15-30° C. The mixture is continuously stirred.

The MBAA solution is added to the mixture of AA, NaOH solution and ice at a temperature of about 15-30° C. while stirring is continued. The beaker that contained the MBAA solution is washed two times with deionized water in an amount of about 10% of the MBAA solution volume per wash. The wash water of both washing steps is added to the stirred mixture.

Deionized water (the remaining amount required to achieve the total amount of (ice and water) of 12639.1 g minus the amount to wash the "V50" containing vessel two times with deionized water in an amount of about 10% of the "V50" solution volume per wash) is added to the stirred mixture, e.g. ca. 3000 g of deionized water.

Then, the resin kettle is closed, and a pressure relief is provided e.g. by puncturing two syringe needles through the septa. The solution is then purged vigorously with argon via an injection needle (e.g. stainless steel 304 syringe, 36 inches long, size 16 gauge from Sigma-Aldrich, # Z152404-1EA) at about 0.4 bar while stirring at about 250-600 RPM. The argon stream is placed close to the stirrer for efficient and fast removal of dissolved oxygen.

After a minimum of one hour and a maximum of two hours of Argon purging and stirring the "V50" solution is added to the reaction mixture at a temperature of about 20-25° C. via a syringe while stirring and Argon purging is continued. The vessel that contained the "V50" solution is washed two times with deionized water in an amount of about 10% of the "V50" solution volume per wash. The wash water of both washing steps is added to the stirred mixture via a syringe through the septa.

After the initiator solution ("V50" solution) is mixed with the reaction mixture, stirring and Argon purging is continued for about 5 min. After that, while the reaction mixture has a temperature of about 20-25° C., two photo lamps (Kaiser ProVision 2.55 HF equipped with 2 lamps Osram Dulux L 55W/830, at max. intensity) are placed on either side of the vessel and switched on. The solution typically starts to become turbid or a sudden increase in viscosity is observed after about 5-20 min, typically at temperatures about room temperature. Then, the argon injection needle is raised above the surface of the gel and purging with argon is continued at a reduced flow rate (0.2 bar).

The temperature is monitored; typically it rises from about 23° C. to about 60° C. within 60 minutes. Once the temperature reaches about 60° C., the lamps are switched off. The reaction mixture can reach for example up to about 80° C. Once the temperature starts to drop (typically temperature starts to drop after about 1-2.5 hours after the reaction mixture reached ca. 60° C.), the resin kettle is transferred into a circulation oven (Binder FED 720 available from Binder GmbH, Tuttlingen, Germany) and kept at about 60° C. for about 20 hours.

After this time, the oven is switched off and the resin kettle is allowed to cool down to about 20-40° C. while remaining in the oven. After that, the gel is removed and broken manually or cut with scissors into smaller pieces. The gel is grinded with a grinder (X70G from Scharfen with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720, equipped with a condensate trap from DAMM (condensation via cooling below dew point via heat exchanger) to dry the circulation air, cooled to 5° C. via a thermostat (Julabo FP 50)) at about 120° C. for about 20 hours.

The residual moisture of the dried gel is typically below 10% by weight, typically in the range of 3-8% by weight.

The dried gel is then ground using a centrifuge mill (Retsch ZM 200 with vibratory feeder DR 100 (setting 50-60), interchangeable sieve with 1.0 mm opening settings, rotary speed 12000 RPM). The milled polymer is then sieved via a sieving machine (AS 400 control from Retsch with sieves DIN/ISO 3310-1 at about 200-280 RPM for about for 5-10 min) to the following particle size cuts:

TABLE 3

| code | BP 1.1 | BP 1.2 | BP 1.3 | BP 1.4 |
|---|---|---|---|---|
| cut | <63 µm | 63-106 µm | 106-150 µm | >150 µm |

Preparation of the Examples and of the Comparative Examples

All experiments are done at ambient conditions of 23±2° C. and relative humidity in the range of 35-61%, typically at 45±10%.

The equipment used is:

ProCell Labsystem Pro by Glatt Ingenieurtechnik GmbH or similar equipment.

Rotor [B205500] with transitional housing [B203001] and cyclone [F121490].

Spray nozzle for tangential spray [V205520]. Nozzle screw position is adjusted to flush with the tip of the nozzle pipe.

Project number: W51505 in 2013.

The system is run without feedback stream of fines from the cyclone.

Pump: Ismatec pump ISM 404B, with pump head ISM 720A.

Hose: silikon peroxid ID=2.06 mm, VWR #228-0704.

Equipment Preparation:

Before the agglomeration is started, the equipment is closed, started and the pressured air valve is opened. The equipment is preheated for about 30 min with air flow of 40 m³/h at 40° C. set point for fluidization air.

The solution preparation (Binder Preparation):

Binder Component A:

In a 600 ml glass beaker (e.g. from VWR, #213-1159) equipped with magnetic stir barr (e.g. elliptic barr of 70 mm length, 20 mm diameter from VWR, #442-0410) and a thermometer for temperature control, 262.1 g PAA solution (polyacrylic acid PAA e.g. 35 w % Sokalan PA 110 S solution from BASF, average molar mass of polymers ca. 250 000 g/mol) is put. Subsequently, 55.6 g of ice (made from deionized water) and 79.2 g of 50 w % NaOH solution (for analysis, e.g. from Merck, #158793, CAS #1310-73-2) are added to the PAA solution such that temperature stays in the range of 25-35° C. The neutralization and subsequent mixing is executed within 30 min.

Separately and meanwhile, 59.7 g of Montmorillonite PGV® suspension in deionized water (solid content about 10 wt %—prepared as described above) is put into a 250 ml glass beaker (e.g. from VWR, LENZ07001049).

Separately, 3.4 g ODD (ethoxylated polyetheyleneimine ODD e.g. Sokalan HP 20, from BASF, CAS #68130-99-4) and 40.1 g deionized water are mixed in a 250 ml glass beaker (e.g. from VWR, LENZ07001049) with a magnetic stir barr (e.g. from VWR, 50 mm length, #442-4528) at about 180 RPM for about 1 min. The stir barr is removed and the water-ODD mixture is added to the Montmorillonite PGV® suspension and stirred for 1 h 25 min to full mixing, with a magnetic stir barr (e.g. from VWR, 50 mm length, #442-4528) at about 180 RPM.

The montmorillonite-ODD-water mixture is added to the neutralized PAA solution and shear mixed till full mixing of components with a 4-blade propeller mixer (e.g. with 40 mm blade diameter, from Sigma-Aldrich, # Z215155) via a stirrer (e.g. IKA® EUROSTAR Power Control-Visc Stirrer) at 900 RPM for 10 min.

Component A is prepared within 24 hours prior to the agglomeration experiment.

Binder Component B:

480.6 g deionized water is put into a glass beaker (e.g. 600 ml beaker from VWR #213-1159) and stirred at room temperature with a magnetic stir barr. 5.36 g of Denacol EX810 (=Ethylene-GlycolDiGlycidylEther=EGDGE, from Nagase, CAS #2224-15-9) is added to the deionized water and dissolved under stirring, e.g. at about 180 RPM. Component B is prepared within 2 hours prior to the agglomeration experiment.

Binder Component C:

In a 600 ml glass beaker (e.g. from VWR, #213-1159) equipped with a magnetic stir barr (e.g. elliptic barr of 70 mm length, 20 mm diameter from VWR, #442-0410) and a thermometer for temperature control, 262.1 g of PAA solution (e.g. 35 w % Sokalan PA 110 S solution from BASF, average molar mass of polymers ca. 250 000 g/mol) is put. Subsequently, 95.7 g of ice (made from deionized water) and 79.2 g of 50 w % NaOH solution (for analysis, e.g. from Merck, #158793, CAS #1310-73-2) are added to the PAA solution such that temperature stays in the range of 25-35° C. The neutralization and subsequent mixing is executed within 30 min.

59.7 g of Montmorillonite PGV® suspension in deionized water (solid content about 10 wt %—prepared as described above) is added to the neutralized PAA solution and shear mixed till full mixing of components with a 4-blade propeller mixer (e.g. with 40 mm blade diameter, from Sigma-Aldrich, # Z215155) via a stirrer (e.g. IKA® EUROSTAR Power Control-Visc Stirrer) at 900 RPM for 10 min.

Component C is prepared within 24 hours prior to the agglomeration experiment.

Preparation of the Binder—Mixing of the Components:

About 10 minutes before starting the agglomeration process, 240 g of Component A (representing the examples according to the invention) or Component C (representing the comparative examples), respectively, are mixed e.g. in a 600 ml beaker (e.g. from VWR, #213-1159) equipped with magnetic stir barr (e.g. elliptic barr of 70 mm length, 20 mm diameter from VWR, #442-0410) with 77 g of Component B. The mixture is stirred for several minutes until full mixing is achieved (e.g. at about 180 RPM).

Agglomeration:

Examples

The equipment is stopped, the slit between the rotary disc and the reactor wall is set to the smallest possible distance (still allowing frictionless rotation and processable pressure differences), opened and charged (e.g. via a stainless steel funnel) with 750.9 g of precursor superabsorbent polymer particles BP 1.2 (63-106 μm cut, see table above).

The equipment is closed, and the equipment is started in the following order at the respective settings:

1) The fan is started, setting 40 m$^3$/h, fluidization air temperature 40° C.
2) The nozzle air is started at 1 bar spray pressure.
3) The rotor is started at 125 RPM.
4) When the fluidization air reaches about 38° C. (typically after about 2 min), the liquid port of the spray nozzle is connected via the hose mounted in the pump head to the binder composition and the pump is started. The binder composition is sprayed at a spray rate of about 3 g/min e.g. at pump setting of about –17 RPM onto the precursor superabsorbent polymer particles BP 1.2 in the reactor.

In total, 317 g of binder composition (240 g of Component A with 77 g of Component B) are sprayed during agglomeration. After that, the pump is stopped while the spray air and the rotation is continued for about 10 min. After that, the equipment is stopped as following:

1) The rotor is stopped.
2) The heater is stopped.
3) The fan is stopped.
4) The spray air of the nozzle is stopped.

The agglomerated superabsorbent polymer particles are removed from the reactor, in total about 792.4 g, and transferred to a baking tray (e.g. Kaiser 7509960, 41×31×10 cm). The tray is covered with aluminum foil and heated in a circulation oven (Binder FED 720) at about 120° C. for about 2 hours 20 min.

After that, the tray is taken out of the oven, the aluminum foil is removed and the tray with the agglomerated superabsorbent polymer particles is allowed to cool down at room temperature for about 1 hour.

After that, the agglomerated superabsorbent polymer particles are sieved via a sieving machine (e.g. AS 400 control from Retsch with sieves DIN/ISO 3310-1 at about 200-280 RPM for about for 5-10 min) to the following particle size cuts:

TABLE 4

| code | Example E1 | Example E2 |
|------|------------|------------|
| cut | 300-850 μm | 850-1250 μm |
| Yield | 468.3 g | 11.1 g |

Comparative Examples

The agglomeration of the comparative examples was done as described for the agglomeration of the examples with the following differences:

Amount of superabsorbent polymer particles BP 1.2: 750.0 g.

Binder Composition corresponds to a mixture of 77 g of component B and of 240 g of component C.

Process stops (limit of differential product pressure was exceeded) 20 min after start of binder spray. Restart of the equipment and spray after 7 min. Further process stops after 5 min of binder spray. Restart of the equipment and spray after 18 min. After that, binder addition for about 1 hour, adding in total 317 g of the binder composition. No rotation continuation after the end of spray.

Amount of agglomerated superabsorbent particles removed from the reactor: 670.8 g.

After heating and sieving, the following materials are available:

TABLE 5

| code | CompEx. C1 | CompEx. C2 |
|---|---|---|
| cut | 300-850 μm | 850-1250 μm |
| Yield | 273.3 g | 25.0 g |

Type of Agglomerated Superabsorbent Polymer Particles:

As indicated in the table below, comparative examples C1 and C2 correspond to agglomerated superabsorbent polymer particles obtained by mixing precursor superabsorbent polymer particles with a solution comprising clay platelets, crosslinkable polymers and a second type of crosslinkers.

Comparative example C1 presents agglomerated superabsorbent polymer particles having a size from 300 to 850 μm.

Comparative example C2 presents agglomerated superabsorbent polymer particles having a size from 850 to 1250 μm.

Examples E1 and E2 according to the invention correspond to agglomerated superabsorbent polymer particles obtained by mixing precursor superabsorbent polymer particles with a solution comprising clay platelets with modified surfaces and/or edges, a second type of crosslinkers and crosslinkable polymers.

Figure 10:
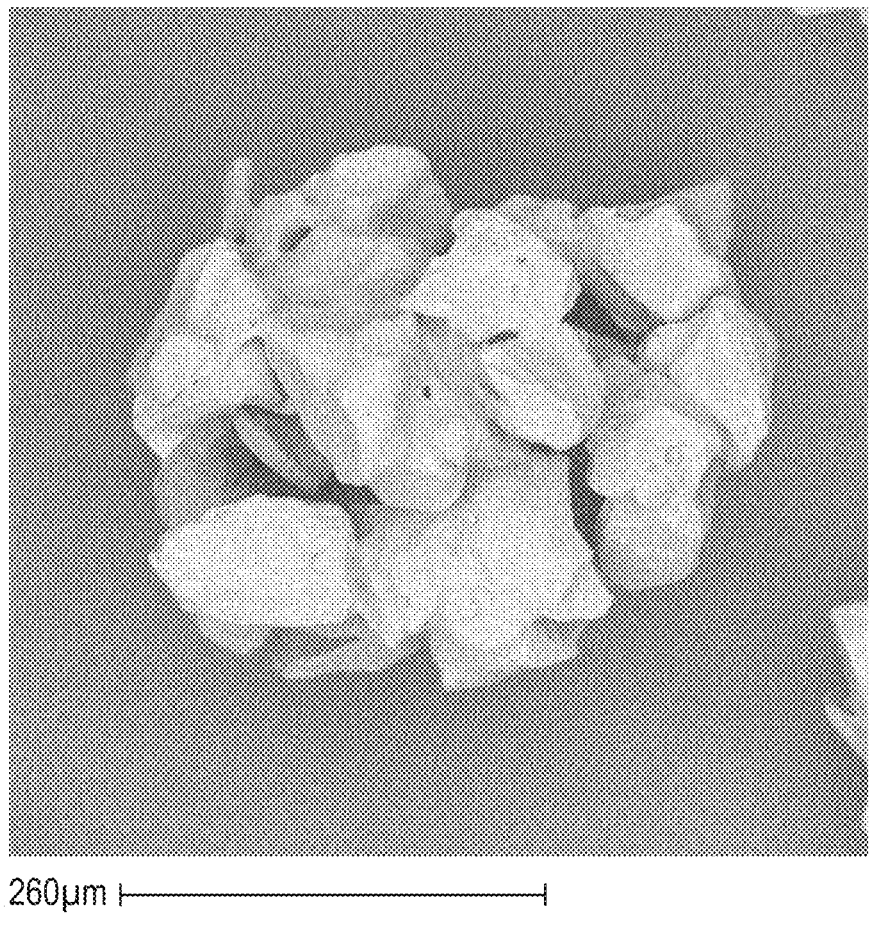
FIG. 10 is a picture of agglomerated superabsorbent polymer particles of example E1 using a Scanning Electron Microscope (SEM).

Example E1 presents agglomerated superabsorbent polymer particles having a size from 300 to 850 μm. FIG. 10 is a picture of agglomerated superabsorbent polymer particles of example E1 using a Scanning Electron Microscope (SEM).

Example E2 presents agglomerated superabsorbent polymer particles having a size from 850 to 1250 μm.

Results:

TABLE 6

| Sample | Comparative Example 1 (C1) | Example 1 (E1) | Comparative Example 2 (C2) | Example 2 (E2) |
|---|---|---|---|---|
| Size | 300-850 μm | 300-850 μm | 850-1250 μm | 850-1250 μm |
| CRC [g/g] | 31.3 | 29.4 | 28.1 | 28.7 |
| FSR [g/g/s] | 1.00 | 1.17 | 0.40 | 0.97 |
| $^1$mAvPS [μm] | 63 | 63 | 63 | 63 |
| $^2$mAvPS [μm] | 422 | 458 | 1036 | >850 |

The agglomerated superabsorbent polymer particles of the invention, i.e. example E1 and example E2, having clay platelets with modified surfaces and/or edges show good performance properties compared to the comparative examples C1 and C2. Indeed, the agglomerated superabsorbent polymer particles of the invention have a good absorption capacity while having a higher absorption speed compared to comparative examples C1 and C2.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Agglomerated superabsorbent polymer particles obtained by a method comprising the steps of:
    a) providing precursor superabsorbent polymer particles having a first mass average particle size $^1$mAvPS, and
    b) mixing the precursor superabsorbent polymer particles with a solution comprising
        i) homogeneously dispersed therein, clay platelets with opposing basal platelet surfaces and platelet edges;
        ii) one or more clay surface modification compound(s) and/or clay edge modification compound(s); and,
        iii) polymerizable monomers and/or oligomers, or
        iv) crosslinkable polymers,
    c) polymerizing the mixed solution if the solution comprises polymerizable monomers and/or oligomers or crosslinking the mixed solution if the solution comprises crosslinkable polymers,
    wherein the clay platelets from step (b) are hydrophilic and are linked to said superabsorbent polymer particles to provide agglomerated superabsorbent polymer particles having a second mass average particle size $^2$mAvPS which is at least 25% greater than the first mass average particle size $^1$mAvPS;
    wherein the agglomerated superabsorbent polymer particles have an average swelling rate to reach 20 g/g of more than 1.00 g/g/s according to the Free Swell Rate (FSR) test method, when the agglomerated superabsorbent polymer particles have a size below 850 μm; and have a Centrifuge Retention Capacity (CRC) value of from 18 g/g to 40 g/g as measured according to the CRC test method.

2. The agglomerated superabsorbent polymer particles according to claim 1, wherein the polymerizable monomers and/or oligomers comprise polymerizable monomers and/or oligomers of acrylic acids or their salts or acrylates or derivatives thereof.

3. The agglomerated superabsorbent polymer particles according to claim 1, wherein the solution comprise a first type of crosslinkers comprising acrylate or acrylamide groups.

4. The agglomerated superabsorbent polymer particles according to claim 1, wherein the solution comprises a second type of crosslinkers being amide acetals, carbamic esters, polyhydric alcohols like dials or polyols, cyclic carbonates, bisoxazolines, epoxides or glycidyl ether.

5. The agglomerated superabsorbent polymer particles according to claim 1, wherein step c) is followed by:
    d) drying the agglomerated superabsorbent polymer particles, wherein the second mass average particle size $^2$mAvPS is determined after step d).

6. The agglomerated superabsorbent polymer particles according to claim 1, wherein step c) is followed by:
  d) drying the agglomerated superabsorbent polymer particles,
  e) classifying the agglomerated superabsorbent polymer particles to obtain a lower particle size limit,
  wherein the second mass average particle size $^2$mAvPS is determined after step e).

7. The agglomerated superabsorbent polymer particles according to claim 1, wherein the precursor superabsorbent polymer particles are subjected to surface cross-linking prior to or simultaneously with step b).

8. The agglomerated superabsorbent polymer particles according to claim 1, wherein the clay platelets are selected from the group consisting of kaolinite, illite, smectite or montmorillonite, or mixtures thereof.

9. The agglomerated superabsorbent polymer particles according to claim 1, wherein the edge modification compound(s) consist(s) of one or more phosphorylation compounds, silanization compounds or fluorination compounds or combination thereof.

10. The agglomerated superabsorbent polymer particles according to claim 1, wherein the surface modification compound(s) comprise(s) an alkylated nitrogen moiety, or alkoxylated nitrogen moiety.

11. The agglomerated superabsorbent polymer particles according to claim 1, wherein the agglomerated superabsorbent polymer particles are surface crosslinked.

12. An absorbent article comprising the agglomerated superabsorbent polymer particles according to claim 1.

13. The absorbent article according to claim 12 comprising an absorbent core, wherein the absorbent core comprises one or more area(s) which is/are substantially free of absorbent material.

* * * * *